United States Patent [19]

Ertel

[11] Patent Number: 5,307,262

[45] Date of Patent: Apr. 26, 1994

[54] PATIENT DATA QUALITY REVIEW METHOD AND SYSTEM

[75] Inventor: Paul Y. Ertel, Chelsea, Mich.

[73] Assignee: Applied Medical Data, Inc., Ann Arbor, Mich.

[21] Appl. No.: 827,376

[22] Filed: Jan. 29, 1992

[51] Int. Cl.$^5$ ............................................. G06F 15/00
[52] U.S. Cl. ........................... 364/413.01; 364/413.02
[58] Field of Search ...................... 364/413.01, 413.02, 364/401, 408, 406

[56] References Cited

U.S. PATENT DOCUMENTS

| | | | |
|---|---|---|---|
| 4,491,725 | 1/1985 | Pritchard | 235/375 |
| 4,591,974 | 5/1986 | Dornbush et al. | 395/100 |
| 4,700,297 | 10/1987 | Hagel et al. | 364/408 |
| 4,857,713 | 8/1989 | Brown | 235/375 |
| 4,858,121 | 1/1989 | Barber et al. | 364/406 |
| 5,018,067 | 5/1991 | Mohlenbrock et al. | 364/413.02 |

*Primary Examiner*—Roy N. Envall, Jr.
*Assistant Examiner*—Khai Tran
*Attorney, Agent, or Firm*—Brooks & Kushman

[57] ABSTRACT

A method and system is provided to review and control clinical data quality in the reporting of hospital claims data. The method and system perform data quality checks and generate turn-around documents that establish communications between coders and physicians in order to obtain the best description of a case for reporting purposes. The system provides file security and tracks cases through the entire review process to final reporting. Patient data and system performance data are aggregated into a common data base. From this integrated data base, a variety of summary reports are generated to identify systematic problems in data quality and to assess the success of the data correction process. The system interfaces with existing data systems to optimize the performance efficiency of a total health information system functioning within a hospital or within third-party claims review organizations including payers of hospital claims.

77 Claims, 7 Drawing Sheets

PATIENT DATA QUALITY REVIEW METHOD AND SYSTEM

TECHNICAL FIELD

This invention relates to methods and systems for reviewing the quality of patient data required on payment claims and, in particular, to computerized methods and systems for reviewing the accuracy, completeness and overall quality of patient data required on hospital payment claims.

BACKGROUND ART

Medicare and numerous other payers have recently converted their reimbursement mechanism to the "prospective payment system". This payment mechanism utilizes diagnosis-related groups, commonly known as "DRG's" to determine the level of hospital payments. Conceptually, DRG's cluster patients to economically homogenous groups, i.e. cases that require comparable resources for their care and that therefore are to receive identical fixed payments. DRG's are assigned by a complex federally-mandated computer program and based upon "case complexity" as conveyed through the configuration of diagnoses reported and/or procedures performed during the course of the hospital stay.

It is the hospital's obligation under federal law to file valid claims statements in seeking compensation for services provided under federal beneficiary programs. Under the DRG-based prospective payment system, the validity of claims statements is dependent upon an appropriate description of case complexity and compliance with reporting requirements since both can affect the DRG assignment and thus the payment received.

There are several tasks that must be performed to enable a hospital to submit an appropriate claim statement for any given case. First, the responsible physician must record and substantiate each diagnosis and procedure term that is relevant to the case, these terms must then be coded in compliance with coding guidelines and reported in compliance with definitional data requirements.

Failure to comply with the conditions described above expose the hospital to two main risks: the risk of inappropriate financial loss and the risk of incurring penalties for misreporting. If the physician fails to describe fully and accurately (and also to document properly) the diagnostic complexity of the case or the full extent of procedural interventions actually performed, the hospital is likely to be inappropriately underpaid. If the diagnosis and/or procedure are inappropriately coded or are otherwise not in compliance with definitional and reporting requirements, the hospital faces potential penalties for filing false claims.

Because data requirements, coding guidelines and reporting rules vary in regard to their specificity, their relevance to the given case, and also with respect to the consequences of non-compliance, the risks which the hospital actually faces can vary in severity from minor to major. Consequently, judgments often must be made as to whether a given case poses risks that are serious enough to warrant the investment of resources necessary to undertake an in-depth case review.

Since there is a strong linkage between the risk of inappropriate financial loss and clinical descriptions of the case in the medical record (i.e. diagnostic and procedural terms recorded), it is appropriate to refer primarily to physicians cases that are at risk of potential financial loss. Because coding practices and definitional requirements are directly linked to misreporting, it is appropriate to refer primarily to coders cases that are at risk of potential penalties.

As previously described, valid DRG-assignments are dependent upon accurate and substantial descriptions of the complexity of a patient's clinical status as documented in the medical record, precise descriptions of procedures performed during the hospital stay, and compliance with established data requirements and coding guidelines in the reporting of hospital claims data.

Consequently, there are two main tasks for third party reviewers such as payers or peer-review organizations to undertake in order to determine whether claims statements that hospitals submit for payment under the DRG-based prospective payment are valid or not.

It is typical of third party organizations responsible for determining the validity of DRG assignments that there is a formal division of responsibility in conducting the record review and data validation process. Typically, case review is initiated by a "review coordinator", usually a nurse. Based upon what is found in the record, the reviewer decides whether there is reason to question the validity of data reported on the payment claim. Cases in which the accuracy of coding is questioned are referred to coding experts or data specialists for final action. In the event that the clinical validity of diagnostic or procedure terms or the adequacy of substantiating documentation is at question, cases of this type are referred to a physician reviewer for final action. Since there is a clear-cut division of responsibility for dealing with clinical as opposed to coding issues, the efficiency of case based review activities is dependent upon routing problem cases to the review personnel who have assigned responsibility for them.

Finally, there is the added dimension that third party review organizations are also responsible for detecting systematic problems in data quality or reporting biases that result in systematic overpayments to hospitals or other care providers. By generating performance profiles from aggregated data, systematic problems in data quality can be detected and related to causative factors. Comparative analyses can be performed across hospitals (and/or other care providers) to establish rational priorities for future in-depth review activities, i.e. to indicate where the investment of personnel and resources would be most productive.

Because there are so many federally-mandated rules and regulations that define the accuracy and validity of diagnosis and procedure terms reported on hospital claims forms subject to the prospective payment system, there is a need for a computer-assisted process designed to promote compliance with these rules and regulations that define the quality of hospital claims data.

The U.S. Pat. No. 4,491,725 to Pritchard discloses a medical insurance verification and processing system which Verifies a patient's insurance coverage, electronically files a claim, converting claim codes as necessary such that the claim is sent to the correct insurance company with the correct claim codes, ensuring the claim will provide payment appropriate for the treatment claimed.

The U.S. Pat. No. 4,667,292 to Mohlenbrock discloses "a computer system for identifying the most appropriate of the billing categories . . . prescribed by a government entity as a basis for determining the amount that health care providers, such as hospitals, are to be reimbursed . . . ". The system includes a process by which billing categories generated by diverse techniques "can be compared by the computer system, . . . if they agree, a high degree of confidence exists in the (selected category) . . . if they disagree, . it is known that a reconciliation must be made . . . this assists the hospital to obtain the maximum reimbursements to which it is entitled."

The U.S. Pat. No. 4,700,297 to Hagel, Sr. discloses a relocation management reporting system which "upon entry of a request for reimbursement the data and expenses category are verified and (stored data) is retrieved and processed to authorize or reject the . . . request."

The U.S. Pat. No. 4,857,713 to Brown discloses "A hospital error-limiting program . . . directed primarily at reduction of hospital errors in delivery of medications, goods, services, or procedures in patient treatment . . . "

The U.S. Pat. No. 4,858,121 to Barber discloses a computerized medical payment system which includes patient, doctor, and carrier verification, and error trapping.

The U.S. Pat. No. 4,591,974 to Dornbush is of a more general interest.

Other Products: Several software products have been or currently are being marketed that deal in a more direct manner with the impact of data reporting on DRG assignments and hospital claims payments than does any of the above-described patented systems. Taken as a group, these newer products share in common a DRG Grouper, files containing diagnoses and procedure codes, files containing defined data error conditions, and a mechanism for generating messages when error conditions are detected in hospital claims data through data edit checks. Some of these products generate a patient data base while others do not. A few generate worksheets to facilitate coder-oriented case review but others do not. The product that methodologically is closest in resemblance to the method and system that is the subject of this application is the Patient Data Quality Manager (PDQM) which was developed by the assignee of this application.

The Patient Data Quality Manager (PDQM) is defined as an integrated set of menu-driven executable computer programs designed to manage the process of improving the quality and accuracy of reportable hospital claims data. It is a stand-alone, microcomputer-based system for processing data quality edits interactively for individual patients.

The principal function served by the PDQM is that of data quality assurance. This function is implemented through a series of interactive transactions supported by an extensive set of Data Quality edits. After the claims data for a given case are key entered into the system, a command is given to run the data quality checks. At the completions of the data quality checking process, any messages generated are displayed on the computer screen. A decision is then made as to whether worksheets are to be generated and printed (in real time or later) to facilitate the human aspect of the data correction process including review of data in the medical record or asking clinicians to provide data not previously recorded.

Worksheets: Two different types of worksheets can be generated: one is formatted to serve the functional needs of data specialists and the other is formatted to facilitate communication with physicians. However, the system operator must personally select the message(s) to be displayed on either type of worksheet.

For example, if a given problem in data quality arises from technical coding issues that can be addressed by the data specialist, a Coding Worksheet can be generated and the system operator selects from a menu the specific message(s) that is (are) to be printed on the worksheet. If the system operator decides that a given data quality message involves clinical judgment or requires additional input from the physician, a Physician Data Quality Worksheet can be generated and the message(s) similarly selected to be displayed on it.

The system is also capable of generating and tracking the Attestation Document that Medicare requires attending physicians to sign for the purpose of verifying claims data. The content of this document is standardized nationwide and contains no data quality messages.

Support Functions: Secondary functions support the logistics of the data correction process, a component of the overall process of improving the quality of reportable hospital claims data. Among the logistic support features of the PDQM are the following:

interactive data entry functions, a data base system containing patient claims data and identifier information on data specialists and physicians, a data archive program that transfers data from closed cases to diskettes for user-selected time periods, certain utility programs that implement user-selected data display options and data base managers to support the basic function of data correction and file maintenance.

While the preponderance of data quality edits contained in the PDQM are proprietary as are all support programs, the program utilizes as sub-routines a number of resources belonging initially to the public domain. Among these are:

DRG Group programs,

ICD-9-CM diagnostic and procedure codes and titles, revised ICD-9-CM codes and titles, other reportable data elements necessary for assigning DRGs, and Medicare edit checks.

A set of security features is also built into the PDQM to protect the confidentiality of patient data.

Log Control Reports: There are several logistic support case listings ("logs") that resemble "tickler" files and contain data essential to determine whether data correction steps for each case have been completed or not or whether there are outstanding data quality worksheets. Other listings are used to assign review cases to specific case review personnel, etc.

In spite of the fact that the PDQM contains a more extensive set of data quality messages and more optional features than is offered by any known competing products, this software package has not been well received in the marketplace and only a few installations have occurred. Many enhancements and user options have been added over a six-year period without materially affecting its marketability. There has also been a relatively high contract cancellation rate for installed systems.

Based on a recent survey of former users, it has been determined the design configuration of the PDQM is flawed. While the intent was to reduce a hospital's risk to both penalties and inappropriate financial losses due to the misreporting of case data, no provisions were made in the PDQM to distinguish one from the other. All messages addressed issues of data quality without classifying them as to reporting risk potential. Neither was any means offered to prioritize cases on the basis of the seriousness of the potential consequences of various types of misreporting. Similarly, while it was also the intent that messages pertaining to inappropriate coding should be transmitted only to data specialists and messages pertaining to clinical documentation problems should be transmitted only to physicians, no built-in mechanism was provided in the PDQM to selectively route these messages to their proper destinations. Message selection was left to operator judgment. Other major deficiencies of the PDQM are that its stand-alone design resulted in duplicated data entry problems for hospitals and its lock-step, operator-dependent, interactive processing of case data was inefficient, resulting in billing delays.

SUMMARY OF THE INVENTION

An object of the present invention is to provide a method and system that utilize the efficiency of batch operations to analyze claims data on entire groups of patients for the purpose of identifying and correcting both case-specific and systematic problems in data quality in the most efficient way possible. Detected problems, which include both actual errors and potential or suspected misreporting, are classified as to potential consequences. The ability to classify messages makes it possible to prioritize individual cases for in-depth review based upon user-defined criteria of importance. Classification of reporting problems with regard to their source makes it possible to automatically route relevant data quality messages to the appropriate recipient personnel. Finally, aggregate data profiles are generated that categorize data quality problems by both type and source, making it possible to identify systematic problems in data quality, intervene appropriately, and monitor subsequent progress over time.

Another object of the present invention is to provide a method and system to improve the accuracy, completeness, and overall quality of patient data reported on hospital payment claims.

A further object of the present invention is to provide a method and system to increase the effectiveness and efficiency of data quality control operations in the preparation of DRG-based hospital claims.

Yet still another object of the present invention is to provide a method and system to enhance the effectiveness and increase the efficiency of review activities directed to assessing the accuracy of data reported on hospital claims and validating the legitimacy of DRG assignments derived from these data.

In carrying out the above objects and other objects of the present invention, a method is provided for automatically detecting, analyzing and classifying the quality of patient data reported on a plurality of payment claims. The method includes the steps of storing collections of patient data including patient identifiers and clinical data, misreporting tables and message tables in data files in memory means and storing classification data and review tables in the data files in the memory means. The method also includes the step of automatically processing a plurality of patient cases. The step of processing includes the case-specific steps for each case of determining whether misreporting and possible misreporting conditions exist in the stored clincial data to obtain determined misreporting conditions; generating at least one data quality message based upon the misreporting tables, the message tables and the determined misreporting conditions; classifying the case based upon the classification data, the review tables and the determined misreporting conditions to obtain classification results; and determining whether misreporting and possible misreporting conditions exist by comparing the classification results with the review tables to obtain additional determined misreporting conditions. The method also includes the steps of displaying via a system output device the patient data including the patient identifiers and the clinical data; displaying via a system output device at least one message based on the determined misreporting conditions in the patient data; automatically accumulating aggregate case data and system analysis data on a plurality of patient cases and storing the aggregate case and system analysis data in the system data files in the memory means; automatically analyzing the aggregate case data to obtain analyzed aggregate case data; and generating at least one analysis report for a plurality of patient cases based upon the analyzed aggregate case data.

Further in carrying out the above objects and other objects of the present invention a system is provided for carrying out each of the method steps and a program storage device readable by a machine and tangibly embodying a program of instructions executable by the machine to perform the method steps are provided.

In one embodiment, the major hospital-oriented functional objectives carried out by the method and system of the present invention are as follows:
- Automated screening of groups of cases (batch mode) to determine the hospital's risk of potential financial loss and the risk of penalty;
- Selectively sorting the problems detected as to their seriousness or priority;
- The generation of appropriate messages that describe both problems in data quality and their solutions in comprehensive terms; and
- Selectively printing on worksheets messages that are appropriate to the individuals responsible for resolving the problems.

In this embodiment the major user-oriented functions of the method and system of the present invention are as follows:
- aggregation of the data quality status reports for a whole group of cases;
- classification of detected data quality problems as to the nature of the risk to which the hospital is exposed (i.e. financial loss vs. penalty),
- generation of summary profile reports that characterize the distribution of data quality problems by type, severity and source in a format suitable for recognizing patterns of systematic data quality problems and suitable also for monitoring the results of the hospital's data correction process.

There are no known automated processes or systems currently in place that implement the major design features described above, at either the case level or at the systems level.

In another embodiment, third party review activities carried out by the method and system of the present invention can be described as follows:
- Automated screening of grounds of cases (batch processing mode) to determine the likelihood of invalid claims reporting on the basis of unsubstantiated clinical descriptors of case complexity and/or non-compliance with established reporting requirements and coding guidelines.

Selectively sorting the problems detected as to their seriousness or priority.

Generation of messages that describe the nature of the data quality problem detected and cite the documentary evidence needed to validate (or invalidate) the data as reported.

Printing messages on worksheets that are appropriate to the professional status of the reviewer(s) responsible for making a determination of data validity.

Transferring of patient data sets from host computer to portable computer in the event that interactive on-site record reviews are to be conducted in hospitals.

In this embodiment, the major user-oriented functions of the method and system of the present invention are as follows:

Aggregating data quality status for groups of cases.

Classifying the data quality problems detected as to their likely cause or source.

Generating a summary profile report that characterizes the likely causes or sources of problems in data quality detected in the group of cases processed. The report format is suitable for providing feedback to the hospital (or care provider) and also for prioritizing future review activities.

Generating a more focused report in a format designed to detect and quantify systematic reporting bias that results in inappropriately increased payments to the hospital or other care provider.

There are no known automated systems currently available that implement the major design features described above at either the case review level or at the systems level.

Other advantages of the present invention will be readily appreciated as the same becomes better understood by reference to the following detailed description when considered in connection with the accompanying drawings.

BRIEF DESCRIPTION OF THE DRAWING FIGURES

BEST MODE FOR CARRYING OUT THE INVENTION

General Description

The method and system of the present invention includes a "main" or "basic" program which, in turn, includes integrated groupings of subroutines plus several utility programs. Also incorporated are several commercially available program modules. The utilities employed in the method and system are primarily stand-alone programs responsive to design considerations pertaining to convenience, flexibility and programming efficiency. The system overall is based upon modular design principles and contains many optional components.

Figure 1A:
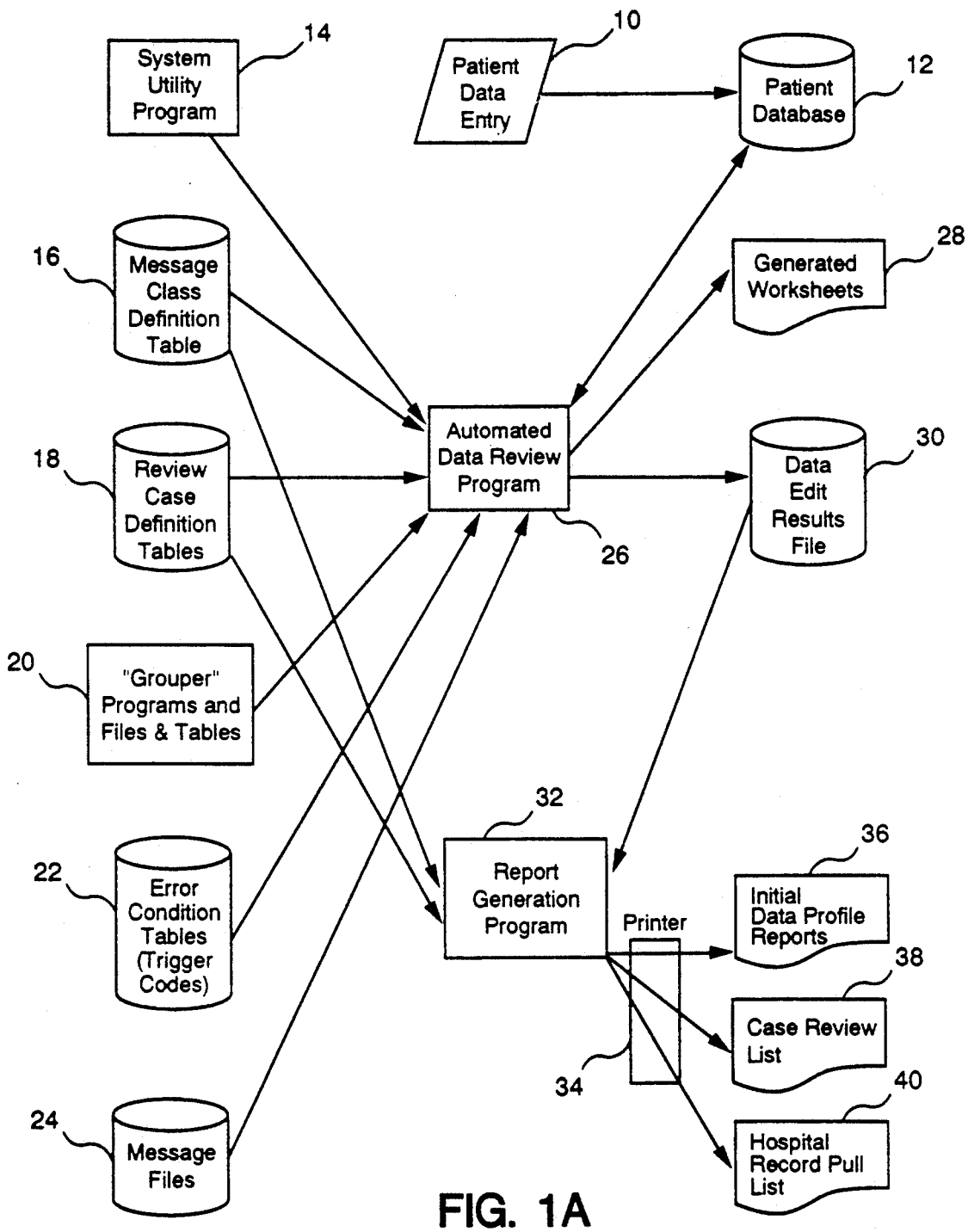
FIGS. 1a through 1c are block diagram flow charts illustrating the system of the present invention.
Figure 1B:
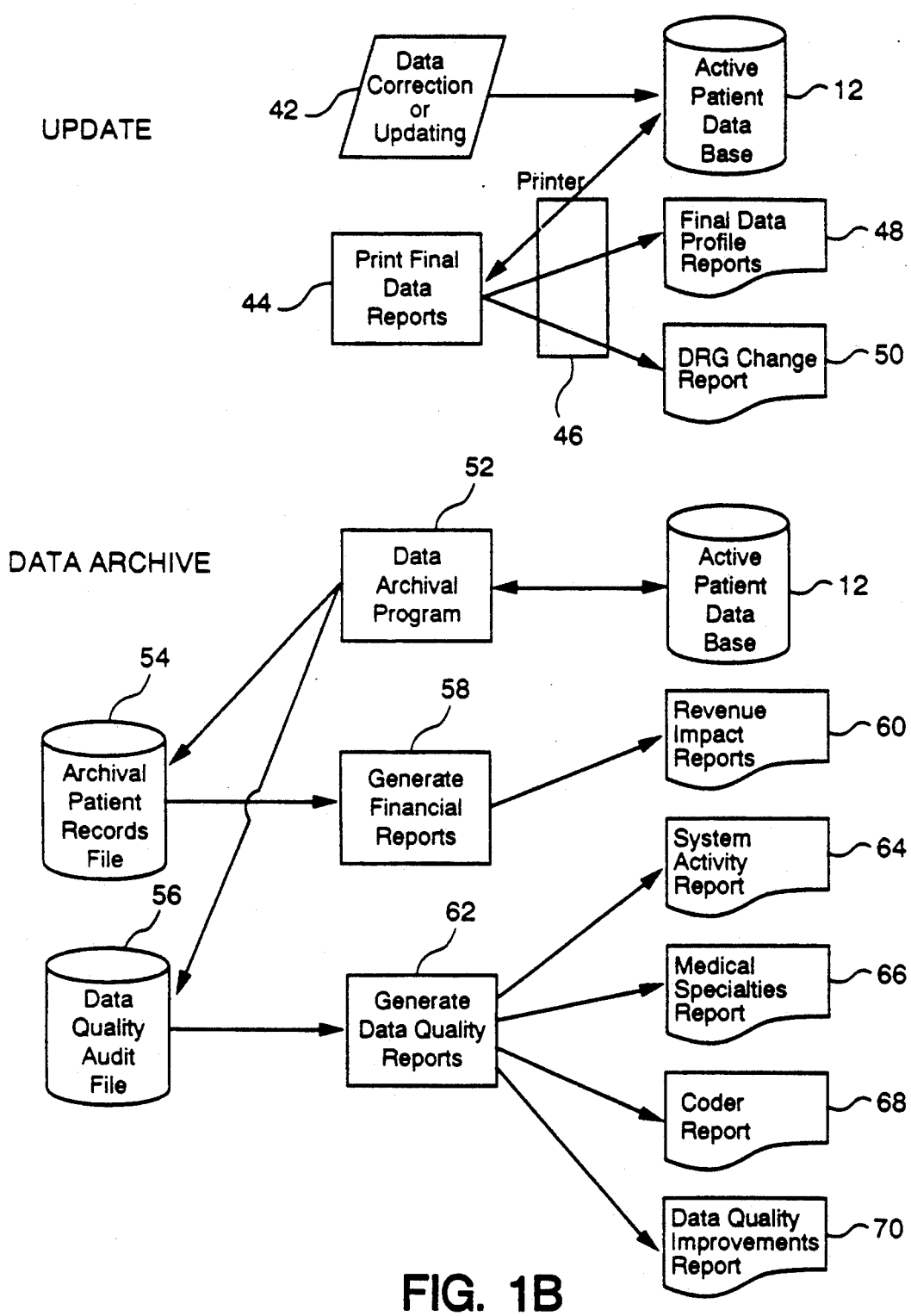
Figure 1C:
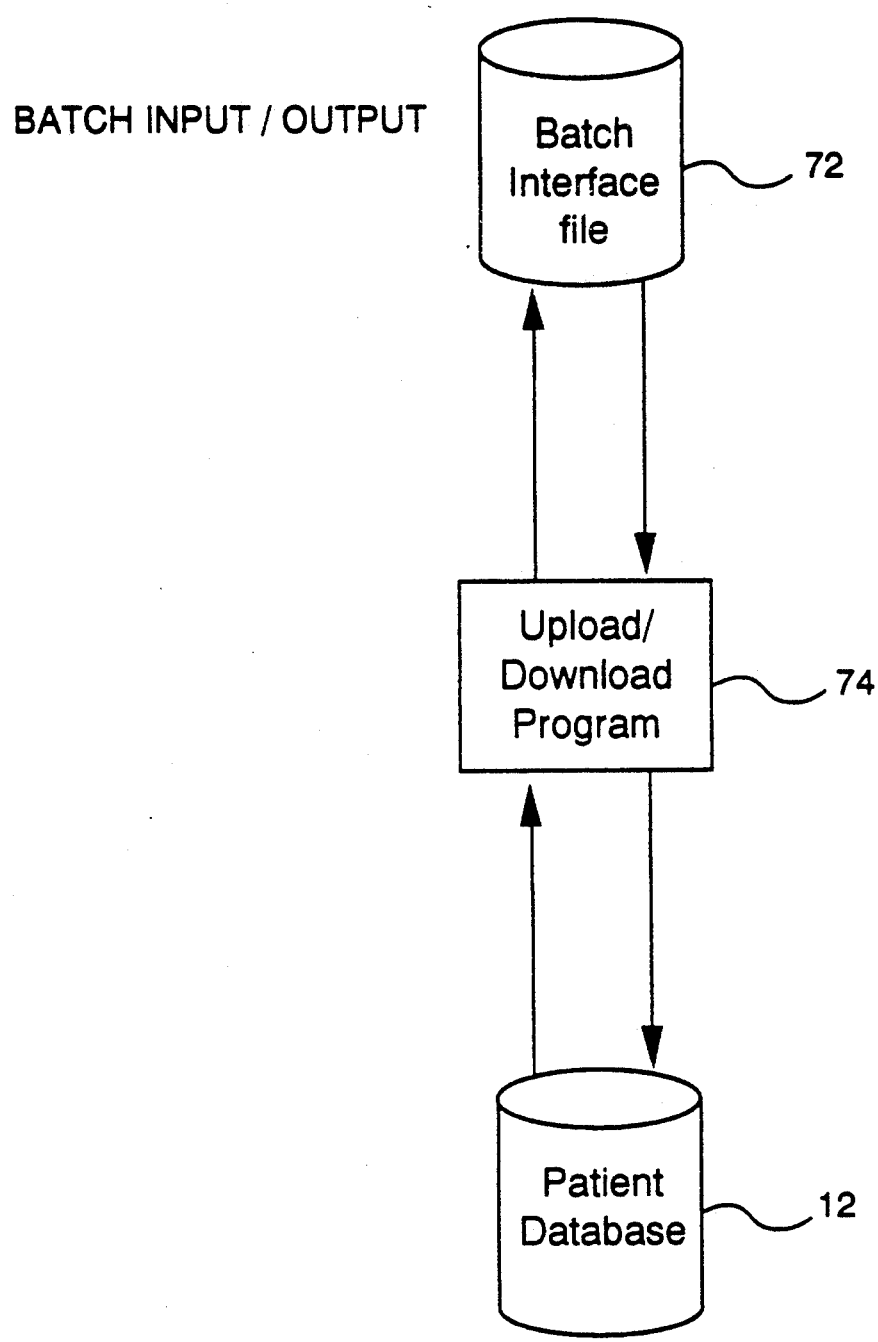

FIGS. 1a through 1c are provided along with their accompanying description to identify all essential components of the overall system and to establish the relationships of the various components to each other. Data processing steps (automated and manual) and associated tangibles such as turn-around documents and output reports are described in these figures of the basic program.

Figure 2A:
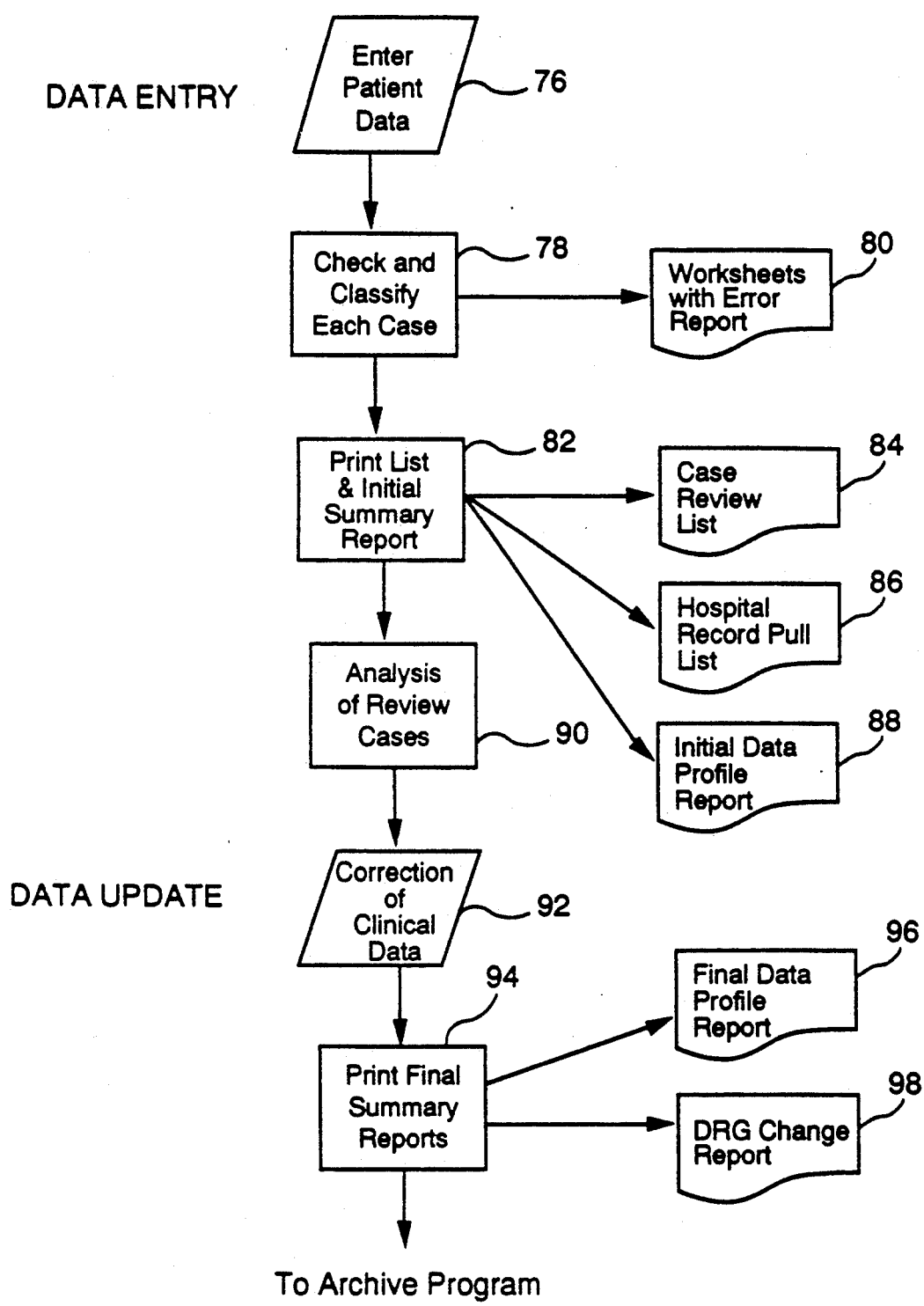
FIGS. 2a and 2b are block diagram flow charts illustrating the method of the present invention.
Figure 2B:
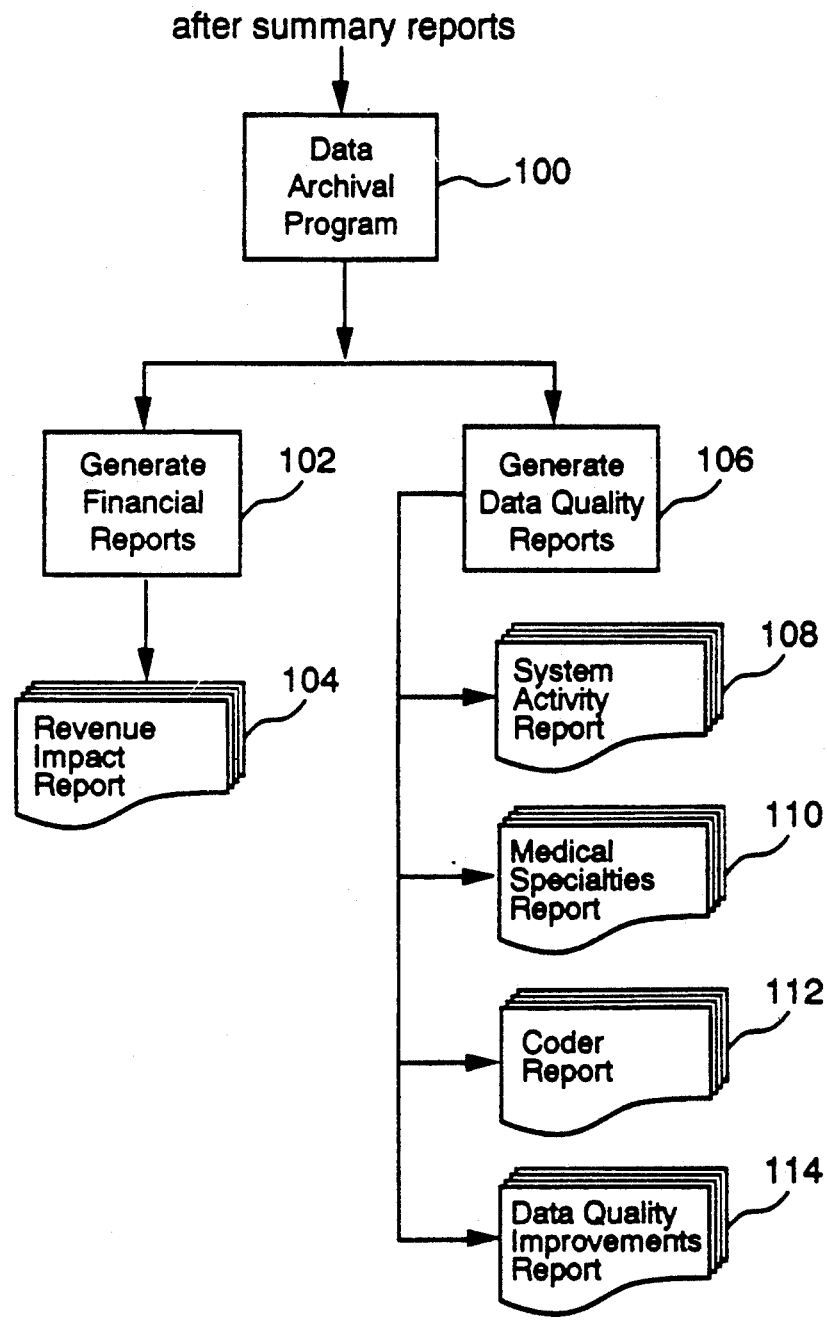

FIGS. 2a and 2b are provided along with their narrative description to depict the actual sequencing of process steps that are necessary to successfully implement the basic program in operational status.

Figure 3:
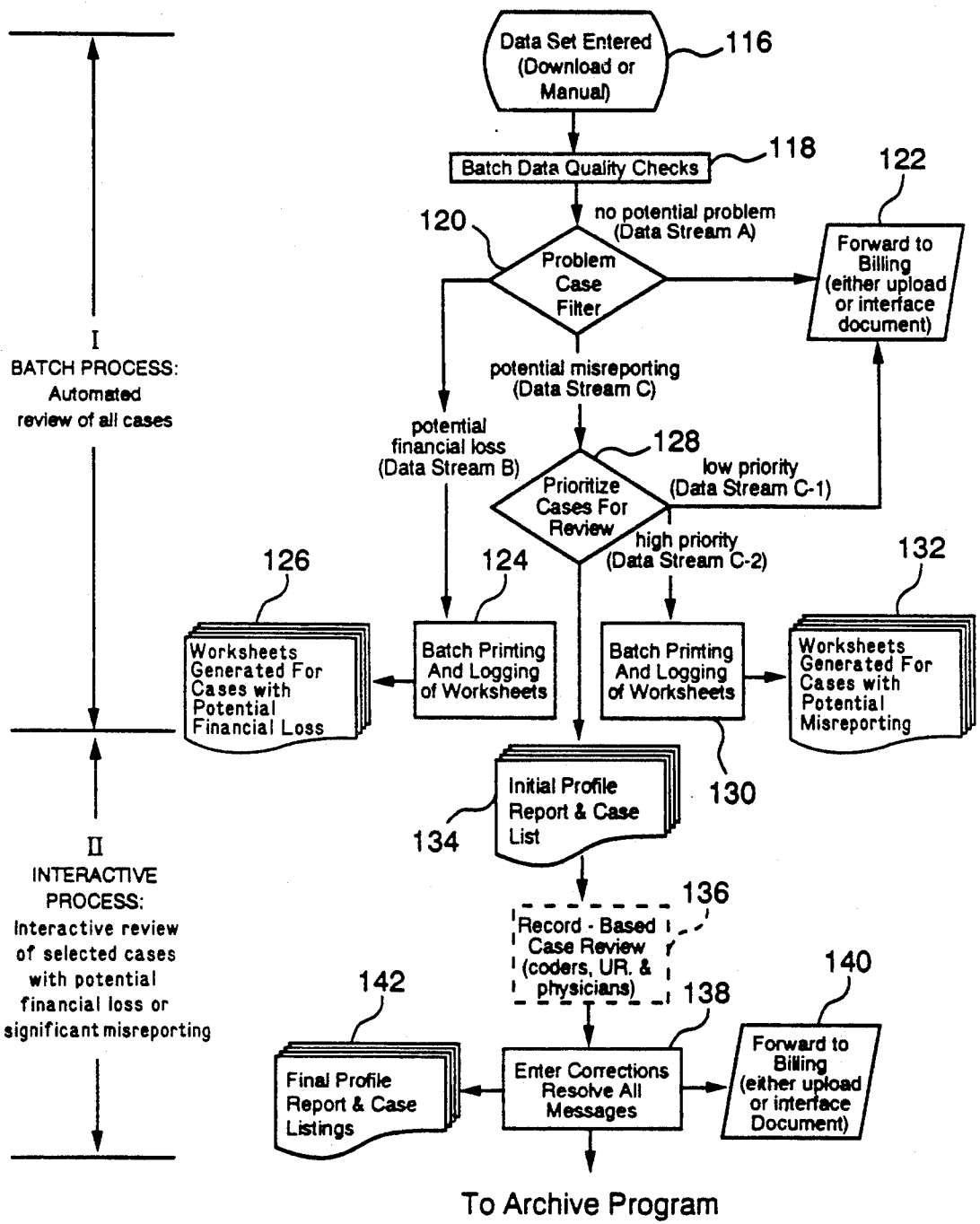
FIG. 3 is a block diagram flow chart of a hospital-based application of the method and system.
Figure 4:
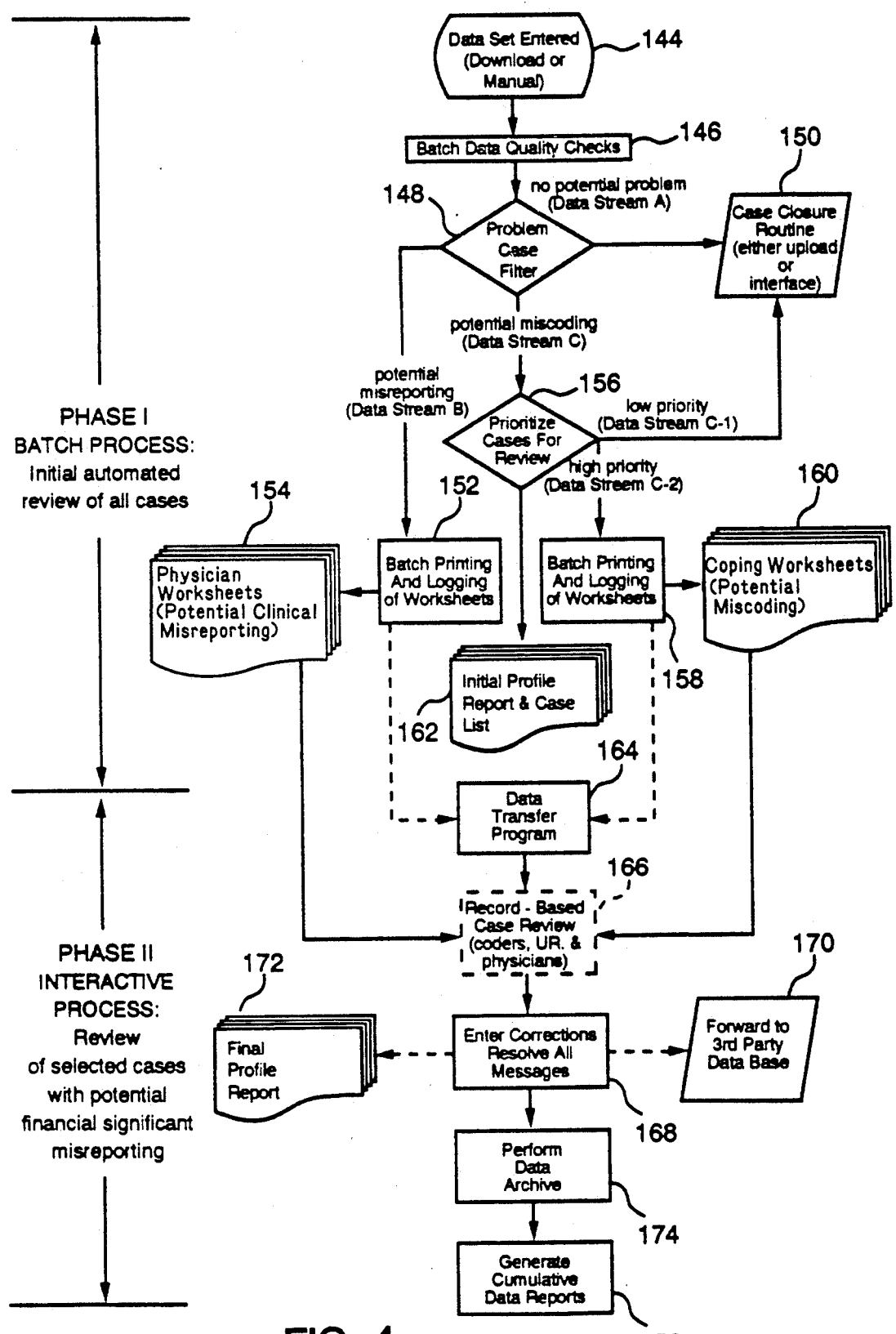
FIG. 4 is a block diagram flow chart of a third party-based application of the method and system.

FIGS. 3 and 4 characterize different combinations of functions in which the basic program is configured to produce products or appliances with differing market applications. For purposes of clarity in describing the functional diagrams, liberal use is made of cross references to relevant features and/or processes cited as components in other drawing figures.

FIG. 3 discloses the hospital-based application of the case processing system and consists of a series of discrete functions that can be divided into two distinctly different phases. In phase I, many manual functions ordinarily associated with the process of screening hospital claims data for the presence of reporting errors are replaced with fully automated functions. Phase II of the data correction process consists of computer-assisted, interactive case review and data correction functions that, by legal mandate, require human input.

FIG. 4 discloses the third-party based application of the data quality review system and is configured to perform a series of discrete functions that conceptually can also be divided into two different phases. The Phase I the preliminary case screening functions that otherwise would be performed manually by a review coordinator are performed in an automated batch operation by the program.

In Phase II, which involves human input to the case review process, many operational steps are computer-assisted, i.e. are typically performed interactively between the reviewer and the automated system.

DETAILED DESCRIPTION OF THE SYSTEM OF FIGS. 1a THROUGH 1c

Block 10, Patient Data Entry

Patient demographic data and clinical data, principally diagnosis and procedure codes, are entered into the patient data base 12. In the event such data are already available on magnetic tape, entry is usually performed in batch mode via a download file using a specified interface file format 72. An alternate embodiment would be to utilize interactive data entry, i.e. one case at a time.

Diagnosis and procedure code tables and the DRG grouper program (which assigns DRGs) 20 are accessed periodically during data entry in order to assign several secondary attributes to patient data sets along with the clinical data actually being entered. Attributes of importance include the DRG assignment, for diagnoses an indicator as to whether they constitute complications or co-morbidities and the DRG-affecting status for procedures.

Precheck of Data Validity: During the download operation, basic data consistency checks are performed on the cases being entered by accessing the patient database interactively. For example, data for a particular patient admission cannot be entered into the database more than once and will be disallowed by the checking process.

Patient demographic information and diagnosis and procedure codes contained in download files are also checked for structural integrity and possible field errors before being entered into the patient data base. All patient records that contain disallowed erroneous data are rejected from the active file and are not further processed. Rejected records are written to a subsidiary file for the purpose of generating a record of the cases that were rejected.

Batch Download Summary: At the conclusion of the batch data download operation, a BATCH DOWNLOAD SUMMARY is displayed on the computer screen that describes the validity status of the data set. A decision could be made to abort further processing at this time in the event that an excessive number of cases with invalid data were detected.

Batch Log Report: A BATCH LOG REPORT is automatically printed that lists all cases downloaded, identifies which cases were rejected, and describes the nature of the data errors found.

Security System: Once data have been loaded into the Patient Database 12, a security system is invoked to protect the entire program, including the patient database, from unauthorized access.

Block 12, Patient Database

Data Content:
Patient identifiers and demographic information;
Clinical data (coded diagnoses and procedures);
Control information for case processing;
Data quality information;
Results of automated and human case processing.

An archival facility 100 is provided which enables case data removal from the active file when case processing is finished. Removed data are stored in historical form on computer media.

Cumulative results of the data edit checking are summarized and added to the stored data for later use to produce profile reports 110 that characterize the quality of the data reported for a given group of cases.

Block 14, System Utility Program

The system utility program is a software component that permits users to pre-set a number of data processing and operational parameters employed in the automated clinical data review program. In effect, this utility permits the user to adapt data processing runs to a variety of review objectives and differing operational conditions. The following user options may be exercised:

Case Selection: Cases may be selected from the patient database for processing through the automated review program on the basis of their data completion status, (i.e. whether they had previously been processed), or based on the source of their claims payment (i.e. payor status).

DRG Grouper Options: A specific DRG Grouper can be selected for all cases in a given processing run, or the option may be exercised to invoke an automatic selection among several groupers on the basis of matching the case discharge date against the implementation date range appropriate to each grouper.

Worksheet selections: Several types of worksheets can be selected that are specifically formatted for relevance to the professional orientation of various review personnel. Identification of the review personnel and care provider (e.g., hospital) which is the source of the review data can be added to each worksheet as additional options. The content and format of the worksheet themselves are also controlled by user options.

Payment Calculations: A provider-specific rate parameter employed in calculating DRG-based hospital payments is entered via the system utility program prior to data processing runs.

Once all system options have been selected by the user and the run command is initiated, all processing steps and outputs from Blocks 16 through 40 are managed through automatic sequencing for the entire group of cases selected for automated review.

Block 16, Message Class Definition Table

During automated data quality edit checking (see Block 26), each case is assigned to a single message class and subclass according to the highest priority message that it generated. The data quality messages are then partitioned into classes and further partitioned into subclasses. This grouping of cases by varying degrees of error specificity enables the user to define (i.e. select) cases that merit further review and analysis by the appropriate personnel and consequently are displayed on Profile Reports 36, 48, 88, 96. A hierarchical ordering is imposed upon the messages' classes based on their priority, i.e. a ranking of importance or severity of the data quality problems addressed by the messages.

Block 18, Review Case Definition Tables

The user defines the criteria by which cases are selected for review. User-chosen criteria can be used to define how review cases are selected. This is done by indicating which message classes or subclasses (as displayed on the Profile Report) will be used to trigger the generation of worksheets and case logs to support the review of medical records and subsequent data correction process.

A case is automatically selected for further review if it contains at least one message in one of the priority classes or subclasses chosen by the user to define a review case. The definitions that establish case review priority are easily reset thus making the system adaptable to changing environments or variations in review objectives that characterize differing types of potential users.

More than one case review definition table can be utilized to screen cases. Therefore, multiple review purposes can be served simultaneously during the automated review process. One example would be the use of review case definition tables that classify generated messages according to the sources of errors or problems in reporting accuracy identified within the hospital claims data. Cases with data quality problems of this type would be of primary interest to third party claims payers or peer review organizations.

Another example is the classification of cases as to their likelihood or risk of incurring financial losses or penalties for the misreporting of claims data. Classifying cases along these dimensions would be of primary interest to care providers themselves, namely hospitals.

Thus, the types of review care definition tables used are key determinants in configuring the basic program into various marketable application packages.

Block 20, The DRG Grouper Program

Utilized as an adjunctive component of the system is the DRG Grouper program developed under Federal contract. This may be defined as a collection of subroutines driven by a set of algorithms and utilizing a variety of data files for the purpose of assigning payment levels to hospital claims.

DRG groupers are either commercially obtainable or are available as public domain documents or software. Some state Medicaid programs and private insurers have also developed modifications of the Federal (i.e. Medicare) DRG grouper. The DRG grouper program used for Medicare patients is updated yearly according to Federal specifications. Multiple versions of the DRG Grouper can be accessed by the main program as needed in order to conform to Federal, institutional, and payer specifications for claims reporting.

A single DRG grouper typically applies to a specific discharge date range and also to a particular claims payer such as Medicare. Several DRG groupers are included in this system and date-appropriate versions are called as subroutines by the main program whenever DRG assignments or the calculation of payments are needed. Other adjunctive components include diagnosis and procedure code tables, DRG assignment number tables, and other subsidiary files including one that contains special attributes associated with diagnosis and procedures.

Block 22, Error Condition Tables

These consist of a collection of files containing error conditions and trigger elements that cause data quality messages to be generated for a given case. Specific conditions or combinations of conditions such as the following are included in these tables:
- certain individual diagnosis or procedure codes
- code combinations
- missing codes (given other conditions)
- patient descriptor-code combinations
- DRG assignments
- DRG-code combinations
- DRG assignment and missing codes

Block 24, Message Files

Short, brief and full text messages are stored in these files and may be displayed on the computer screen and/or printed on worksheets 28 for each data quality edit that produces a message for a given case.

Block 26, Automated Data Review Program

Numerous data quality check subroutines are run automatically in batch mode on the clinical data in combination with other patient data for each case.

Data Check Subroutines: The purpose served by data check subroutines is to generate prompt messages that are designed to assist responsible personnel in complying with a wide range of informational requirements and coding guidelines in the process of preparing hospital claims reports.

Data Checking Process: Clinical and other relevant patient data are edited by a process in which the data element being checked is compared against a specified list of disallowed values or error conditions. If there is a match between the case data entered (such as a diagnosis or procedure code) and the error conditions listed for that data field, then the case fails the given data edit check and a data quality message will be generated at the appropriate time in the processing cycle.

Error Conditions: Trigger files and tables contain error conditions to be identified during the data checking process. Principally, the trigger elements consist of lists of diagnosis and procedure codes, patient descriptors such as age and sex, and DRG assignments. The specific arrays of data elements that trigger message generation are listed under block 22.

Message Types: Some data quality messages are generated that describe data entry errors, coding errors, and other "actual" (i.e., absolute) reporting errors that are in non-compliance with explicit requirements or published guidelines. Messages of this kind cite the relevant official rules and indicate what must be done to comply with them. Other messages describe possible or "potential" problems in data quality such as the apparent underreporting or overreporting of case complexity. Messages of this kind convey suggestions for increasing the accuracy of clinical descriptions and cite legitimate alternatives for reporting the involved data elements. Both actual errors and potential data quality problems are detected during the same data quality checking process. The full scope of message types is cited below.

Scope of Data Quality Edits

1. Documentation Requests
2. Coding Alerts
3. Incomplete Abstracting
4. Unsubstantiated Data
5. Underreporting
6. Resource Utilization
7. Reporting Reminder
8. Inappropriate Billings
9. Pro Alerts General Message Construction: The typical data quality message will describe the nature of the problems in data quality detected and offer suggestions for their resolution. Typically also, a header statement identifies what clinical term or other data element triggered the message. Shown below is an example of how full-text data quality messages appear on review worksheets.

| CODING ALERT | [ ] CODER |
|---|---|
| Term A (Preliminary Dx1) : NORMAL DELIVERY | 650 |
| Term B (Procedure) : FETAL MONITORING NOS | 7534 |
| "Normal Delivery" incompatible with Px. OB condition for which Px performed is more appropriate as Dx1. (Coding note: when OB Dx given, delete 650.) [OCG 2.16] | |

Short, brief and full-text messages are available for each edit check. The content length of messages displayed or printed is dependent upon the appropriateness of detail to the recipient review personnel. Usually, coders prefer to receive the short messages in screen displays. Some physicians prefer brief messages and others prefer to receive full-text messages printed on worksheets.

A number of tables are utilized for look-up functions during the operation of data quality subroutines. These tables are described below.

Review Definition Tables 18 are accessed as needed to determine whether the case contains an error message of sufficient severity to warrant further personal review and thus generate a worksheet to convey the message(s) to the appropriate personnel. Typically, the presence of any actual error would define a review case but only certain potential reporting problems would, depending upon the purpose of the review process.

Diagnosis and procedure tables 20 contain descriptive information related to reportable ICD-9-CM diagnosis and procedure terms. Items include the English title, the code number associated with the title, whether a code is complete or incomplete, the number of digits in the code, etc.

A DRG Table 20 contains similar descriptive information for DRG assignments. Items include the English title, the DRG assignment number, the cost weight (i.e. payment factor associated with the DRG) and other related information.

Another table 20 stores official changes made to codes or titles that are contained in new versions of the ICD-9-CM coding manual. Similarly, revisions made to DRG titles and DRG assignment numbers used by the DRG grouper are contained in an additional table 20.

Results of the entire data checking process for each case are written to an "Edit Results" file 30. Review worksheets containing prompt messages resulting from failed edits are also generated during the batch run as described at block 28.

Block 28, Generated Worksheets

Worksheets (turn-around data correction documents) are optionally generated for all cases or for designated review cases only. See Tables 1A and 1B for samples of worksheets. The type of worksheet to be generated is pre-selected by the user before the batch run is initiated. This pre-selection will determine what type of worksheets are to be generated for various types of review cases (and/or for non-review cases as well).

Worksheet Content: The informational content of worksheets includes case identification information and care provided information in addition to the data quality messages. Also included are instructions to promote compliance with the messages and pre-structured data entry fields for recording data corrections.

Messages: any message may be selectively addressed to nurses, review coordinators, coders, or physicians based upon the relevance of message content to the expertise of the recipient. The intended recipient is cited in the header. These selections can be pre-set in the system utility program 14 to identify and sort messages for printing on worksheets dedicated for use by various personnel.

Worksheet logging and tracking subroutine: As each worksheet is generated, it is automatically assigned a log number (if this option is implemented in the setup utility). Worksheets are then tracked until completion. Logging all worksheets back into the system becomes a condition for case closure and for its removal from the active file through the archive process.

Block 30, Data Edit Results File

One record is created in the data edit results file for each case processed through the automated data review program 26. This "results file" is used primarily for report generation.

The record contains:
patient identifier information
data quality message numbers generated for the case
initial and final DRG assignments and cost weights
identifier of grouper version used
review-class assignments
Header and trailer records include:
dataset or batch identifier information
number of cases processed
selected option settings
review events timing data

Block 32, Report Generation

Several reports are generated from the Data Edit Results File 30, such as by a printer 34. These include data summaries or "profile" reports 36, a review case assignment list 38 which is categorized by error class, and a record pull list 40 to provide logistic support for the review process. Review Definition 18 and Class Definition Tables 16 are accessed during the course of report generation in order to configure case data into the formats called for in these reports.

Block 36, Print Initial Data Summary Reports

The initial Data Quality Profile Report (also known as a "diagnostic profile" report) is generated at the beginning of the review process. This report contains percentages and counts of cases in each hierarchical category of data quality messages (see Table 2). The hierarchical distribution of message types on this report conveys information useful to the process of selecting review cases.

In the event a case generates multiple messages, it is assigned only to the category of the message with the highest priority, i.e. in the highest hierarchical classification order.

Included in one version of this report as a supplementary data column are percentages and numbers of cases with diagnoses and/or procedure codes sequenced to achieve maximum payments under the DRG-based payment mechanisms (see Table 3). Data in this column reveal the extent to which correlations exist between erroneous data reporting and maximal DRG-based claims payments.

Optionally included is a "Veracity Index" which is a surrogate measure of reportorial honesty in other aspects of claims reporting. It is calculated as a ratio of the number of edits that identify unexploited opportunities to increase hospital payments (i.e. potential under-reporting) divided by the total number of edits applicable to the entire group of cases.

Other optional summary reports that could be generated from initial (i.e. uncorrected) data include a variety of data quality status reports by coder or by physician specialty.

Block 38, Case Review List

This printed list (see Table 4) contains cases sequenced by review category and subcategory. Categorization is performed on the basis of the highest priority message content generated for each case and referred to as "data quality status".

Block 40, Hospital Record Pull List

This list (see Table 5) itemizes each review case that was selected by the user's choice of message classes for initiating the generation of worksheets and conducting subsequent review activities.

Block 42, Data Correction or Updating

Data changes (corrections or updates) may be entered into the patient data base 12 either via batch download form another data management system or manually through an interactive mode. Database consistency, initially checked when changes are entered via batch download, is again checked automatically at the conclusion of all interactive data changes made for each case.

An interface file 72 has been provided to transfer corrected case data between the Patient Database 12 and the upload/download program (see block 74). Several different record formats are incorporated into this film which lends flexibility in adapting the program for varying uses and environments.

Block 44, Print Final Data Summary Reports

Once patient data have been corrected, a second (i.e. followup) data set is created that permits the generation of data comparison summary reports, such as by a printer 46. Not only is it possible to contrast the quality of initial versus final (i.e. corrected) data, it is also possible to calculate the impact of the overall data correction process on hospital-based payments. Described below are two types of reports that are considered to be standard output of the system.

Block 48, The Final Data Profile Report

This report is printed after the medical records for a batch of cases have been reviewed and relevant corrections have been made to the data set. The report may be generated either from the patient database 12 or from archived data as is described in the Process Diagram (see FIGS. 2a and 2b). The general content of the report is identical to that seen in Initial Data Summary Reports (see Table 2). The distinctions are that this report is processed from corrected or "final" data and an additional column may be added as an option to display the differences between initial and final data. Cases can be selected for inclusion in the report by a range of hospital discharge dates.

Block 50, A DRG-change or "Revenue Impact" Report

This report is generated (see Table 6) from final data in the active patient data base 12 (it can also be generated from archived data as described at block 74). This report is comprised of two parts:
 a case-by-case list of changes in DRG assignments and associated payment rates, and
 an overall summary of the financial impact of the entire review process.

For a description of the process by which these reports are generated, see block 100 in the Process Diagram (FIG. 2a).

Block 53, Data Archival Program

During data archival operations, patient records are removed from the active patient database 12, stored on archive media 54, and also added to a cumulative archival audit (i.e. historical) database 56. Two differing families of reports are generated from archived data files as is explained below.

A preview of case completion status displays the number of "closed" (i.e. completed) records for discharged patients and also the number of "open" cases and current inpatients for all appropriate months. The system operator normally would review the completion status of case records entered into the data base in the interval since data were last archived. This allows the system operator to select the time period for the current archive session based upon a desired level of record completions.

Block 54, Archival Patient Records File

Several different categories of data are archived and accumulated in the archival patient records file. These include patient demographic data, hospital stay data, discharge data, clinical data, financial data, data-quality status data, and personnel performance data (physician turn-around time, physician cooperation, coder accuracy and proficiency, etc.)

Archival data are written onto transportable media, such as floppy disks or magnetic tape. These media-stored data are routinely used for generating financial impact reports (see block 100). Another potential use for these data involves contingent case retrieval, i.e. to re-activate case files under special conditions such as data loss, delayed record updates, or for reassessing data quality for special studies.

Block 56, Data Quality Audit

Information pertaining to data quality is routed during the archival process to the Data Quality Audit file which is actually a subset of the Archival Patient Record File 54. Longitudinal data are accumulated in this file and organized in a format that facilitates the generation of a variety of data quality reports typified by the System Activity Report as indicated at blocks 62 through 70 (see Table 7).

Block 72, Batch Interface File

The Batch Interface File 72 is used to import and export data into and out of the Patient Database 12 via an Upload/Download batch operation 74. Several record types, each containing a different subset of the overall patient database, are made available to the data transfer operation. Any collection of record types may be accessed during a batch upload or download operation. The ability to select various mixes of record types contributes to a high degree of flexibility in utilizing the Upload/Download operation 74 for a variety of differing purposes.

The data entering the interface file are checked for format, content, and database consistency. A report may be generated to identify errors and to list by case all successful data transfers. Records found to be in error are written to a reject file.

Block 74, Upload/Download Program

This component of the program transfers patient data in batch mode between the Patient Database 12 and the Upload/Download Interface File 72. It incorporates the ability to test the validity of download data and generate transaction reports. Its primary uses are to download data in batch mode into the Patient Database 12 of the main program and maintain database consistency.

The Upload/Download program permits the transfer of patient data between a microcomputer containing the Patient Data Quality Review System and mainframe computers or external devices via PC-DOS floppy disks or by any method able to access a PC-DOS file. Data transfer can occur in both directions and the method employed is capable of supporting both concurrent and retrospective hospital review systems.

To effect the data transfer functions involved in upload/download operations, some computer programming must be written to link the Patient Data Quality Review System with other software employed by the "host" (i.e., mainframe) computer.

Download Capabilities: In the overall download process, patient data are transferred from a mainframe computer into the Batch Interface File 72 (download file). The download program then transfers the contents of that file into the Patient Data Quality Review System Database 12. The integrity of all data in the download file is checked. Cases that fail any integrity checks are rejected and a copy of each record comprising the case is written to the "reject file." A Download Log Report is generated upon completion of the download process. This log identifies the disposition of each case in the data set. The reason for any case rejection appears in this log.

Upload Capabilities: The Upload program transfers patient data from the Patient Data Quality Review System database 12 to the Batch Interface File 72 (upload file). From there, case data are transferred via a linkage system to the mainframe computer. Interfaces between medical record review operations and other data systems are enhanced by uploading data elements essential for making DRG assignments and other external reporting requirements. An Upload Log Report is generated upon completion of the upload process to provide a list of the cases that have been uploaded.

TABLE 1A

| CODING WORKSHEET COMMUNITY GENERAL HOSPITAL | | PT ID# NAME SEX AGE | 10095051 Doe, John Male 087 years |
|---|---|---|---|
| PHYS ID# | 01 | ADM DATE | 11/07/90 |
| NAME | Ima GoodDoctor | DIS DATE | 11/12/90 |
| LOCAT | | DISPOS | 1 |
| PHONE | | PAYOR | 1 |
| SERVICE | SURG | REPORT DATE | 07/02/91 |
| CODER ID# | 01 | WS# | MR 616 |

CURRENT DATA

| Prelim Principal Diag: | 5997 | x | HEMATURIA |
|---|---|---|---|
| Secondary Diagnoses: | 496 | C | CHR AIRWAY OBSTRUCT NEC |
| | 5934 | | URETERIC OBSTRUCTION NEC |
| | 2859 | | ANEMIA NOS |
| | 59389 | | RENAL & URETERAL DIS NEC |
| | V1052 | | HX OF KIDNEY MALIGNANCY |
| | V446 | | URINOSTOMY STATUS NEC |
| Procedures Performed: | 8773 | | INTRAVENOUS PYELOGRAM |

CURR DRG: 325 Kidney, urinary signs, Sx >17 w CC Wt: .6666
DATA QUALITY MESSAGES: Review all messages before changing data.
UNDERREPORTING? [ ] PHYS
Preliminary Dx1: HEMATURIA   5997
Symptoms or signs are NOT to be reported as Dx1 FOR INPATIENTS unless unable to diagnose chief reason for admitting patient. The CAUSE of the symptom or sign should be reported as Dx1. Differential diagnoses or presumptive diagnoses qualified as "probable", "suspected", "likely", "questionable", "possible" or "still to be ruled out" are preferred over the reporting of symptoms or signs. (Coding note: Qualified terms are to be coded the same as established diagnoses. The symptom or sign may be reported as a Dx2). [OCG 2.1]
UNDERREPORTING? [ ] PHYS
Preliminary Dx1: HEMATURIA   5997
Insufficient reason for admission unless operated on for this condition. Note: association of Dx1 as the indication for the inpatient surgical Px must be documented explicitly in final note, discharge summary, or face sheet. [OCG 2.9]

PT ID#   098653
WS#   MR 606   07/02/91

ACTION BY MEDICAL RECORDS DEPARTMENT
(Check one of three boxes on left)
1. ( ) One or more messages are relevant; revisions

TABLE 1A-continued are indicated below. Revise input and re-run data quality checks.

| Items Questioned | Change to __ | Add __ | Delete | Swap With __ | Move to |
|---|---|---|---|---|---|
| Dx1 | 7802 | | XXXXXXX | | XXXXXX |
| Dx2 | 5990 C | | | | |
| | 2765 C | | | | |
| | 92303 | | | | |
| | 9140 | | | | |
| Px | 8703 | | | | |

2. ( ) Revisions may be needed but require physician input; generate physician sheet.
3. ( ) None of the data quality messages apply to this case; delete messages.

TABLE 1B

| PHYSICIAN'S DATA QUALITY WORKSHEET COMMUNITY GENERAL HOSPITAL | | PT ID# NAME SEX AGE | 10095051 Doe, John Male 087 years |
|---|---|---|---|
| PHYS ID# | 01 | ADM DATE | 11/07/90 |
| NAME | Ima GoodDoctor | DIS DATE | 11/12/90 |
| LOCAT | | DISPOS | 1 |
| PHONE | | PAYOR | 1 |
| SERVICE | SURG | REPORT DATE | 07/02/91 |
| CODER ID# | 01 | WS# | PR 614 |

CLINICAL DATA: Review the current data and data qualtiy mesages before changing data. RE-NUMBER the sequence of diagnoses or procedures if appropriate; indicate AGREEMENT, or make appropriate CHANGES. Documentation in the medical record should be consistent with re-sequencing, changes or additions.

PRINCIPAL DIAGNOSIS

| (Diagnosis explaining admission) | | (check box) AGREE | DIS- AGREE | (write-in) CHANGES/ ADDITIONS |
|---|---|---|---|---|
| 1. HEMATURIA | 5997 | X ( ) | ( ) | |
| Secondary Diagnoses | | | | |
| 2. CHR AIRWAY OBSTRUCT NEC | 496 | C ( ) | ( ) | |
| 3. URETERIC OBSTRUCTION NEC | 5934 | ( ) | ( ) | |
| 4. ANEMIA NOS | 2859 | ( ) | ( ) | |
| 5. RENAL & URETERAL DIS NEC | 59389 | ( ) | ( ) | |
| 6. HX OF KIDNEY MALIGNANCY | V1052 | ( ) | ( ) | |
| 7. URINO-STOMY STATUS NEC | V446 | ( ) | ( ) | |

PRINCIPAL PROCEDURE
(Most related to reason(s) for admission)

| 1. INTRAVENOUS PYELOGRAM 8773 | | ( ) | ( ) | |
|---|---|---|---|---|
| Physician: 01 Op Date: 11/09/90 | | ( ) | ( ) | |

CURR DRG: 325 Kidney, urinary signs, Sx >17 w CC Wt: .6666

| HOSPITAL STAY: (days) | Average 4.4 | Outlier Status 33 | Stay to Date 5 |
|---|---|---|---|
| | | PT ID# | 152232 |
| | | WS#   PR 607 | 07/02/91 |

DATA QUALITY MESSAGES: Review all messages before changing data.
DOCUMENTATION REQUEST [ ] PHYS
Secondary Dx: ATRIAL FIBRILLATION 42731
As presently reported, this case qualifies for a DRG

TABLE 1B-continued assignment based upon the presence of a C.C. The above secondary diagnosis reported as the only C.C., however, is either vague or a laboratory finding. To be reported legitimately, there must be documentary evidence of the relevance of this condition to case management or the hospital stay. If clinically supportable, an etiologic diagnosis is preferred. (Coding note: If etiologic diagnosis is precluded, the reporting of this term must be acceptable to the attending physician and be explicitly substantiated on the medical record.) [OCG 3.5] SUBSTANTIATING DATA? [ ] PHYS
Preliminary Dx1: PARALYTIC ILEUS 5601
DRG: 180 Gastrointestinal obstruction with cc
Cost Weight: .9165
If any of the Dx2(s) listed below is more relevant or in combination with above Dx was CHIEFLY RESPONSIBLE for
the admission, consider as Dx1. Documented circumstances of the admissions determine the choice of Dx1 and both differenctial and presumptive diagnoses are acceptable for INPATIENT reporting purposes. Presumptive diagnoses may be qualified by descriptors such as "possible", "likely", or "probable", etc. [OCG 2.5, 2, UHDDS]
Alternative Dx1: ATRIAL FIBRILLATION
42731 DRG:138 .8331
Alternative Dx1: DIVERTICULITIS OF
COLON 52211 DRG: 182 .7497
Sources of rules cited in brackets are available upon request.
WORKSHEET DISPOSITION: 
FOR QUESTIONS OR ASSISTANCE,
CONTACT: Ima Goodcoder
Phone:

TABLE 2

Report data: 12/20/90
QuickScreen DIAGNOSTIC PROFILE
Hospital: MEDICAL CENTER
Payor: ALL
Grouper Used:            Date Range:

| Review Categories | No. of Cases | % of Tot | Present Revenue |
|---|---|---|---|
| TOTAL CASES SCREENED | 32 | 100.0 | |
| NO PROBLEMS | 7 | 21.9 | |
| DATA QUALITY STATUS* | | | |
| 13. Coding Alert-Financial | 1 | 3.1 | $ 18368 |
| 13.1 Medicare Edits | 0 | 0.0 | |
| 13.2 Other Financial Edits | 1 | 3.1 | |
| 12. Coding Alert-Penalty | 4 | 12.5 | $ 11094 |
| 12.1 Medicare Edits | 3 | 9.4 | |
| 12.2 Other Penalty Edits | 1 | 3.1 | |
| 11. Incomplete Abstract? - Financial | 5 | 15.6 | $ 59525 |
| 10. Incomplete Abstract? - Penalty | 0 | 0.0 | |
| 9. Documentation Request - Financial | 8 | 25.0 | $ 55962 |
| 8. Documentation Request - Penalty | 0 | 0.0 | |
| 7. Substantiating Data? - Financial | 3 | 9.4 | $ 14539 |
| 7.1 Alternative Dx1. Med | 2 | 6.3 | |
| 7.2 Alternative Dx1. Surg | 1 | 3.1 | |
| 7.3 Other Financial Edits | 0 | 0.0 | |
| | 0 | 0.0 | |
| 6. Substantiating Data? - Penalty | 1 | 3.1 | $ 6352 |
| 5. Underreporting - Financial | 3 | 9.4 | $ 13835 |
| 5.1 Possible Missing CC | 0 | 0.0 | |

TABLE 2-continued

Report data: 12/20/90
QuickScreen DIAGNOSTIC PROFILE
Hospital: MEDICAL CENTER
Payor: ALL
Grouper Used:            Date Range:

| Review Categories | No. of Cases | % of Tot | Present Revenue |
|---|---|---|---|
| 5.2 Other Financial Edits | 3 | 9.4 | |
| 4. Underreporting? Penalty | 0 | 0.0 | |
| 3. Resource Utilization?- Financial | 0 | 0.0 | |
| 2. Resource Utilization?- Penalty | 0 | 0.0 | |

*Note:
Problem cases are assigned to only one data quality status catergory and are ranked sequentially from the highest to the lowest priority. Any case with multiple data quality messages will be counted only once in the highest ranked priority category.

TABLE 3

MAXIMONITOR PRE-REVIEW DIAGNOSTIC PROFILE
(Priority sequenced for selecting review cases)

Hospital: OPRS TEST RUN - 8/22/91
Payor: All    Date Range:
Base Rate: 1000   Grouper Used: 8.0

| | Maximized Cases | | Total Cases | |
|---|---|---|---|---|
| | # | % of Tot | # | % of Tot |
| A. Cases Screened: | 91 | 42.1 | 216 | 100.0 |
| B. No Problems | 0 | 0.0 | 2 | 0.9 |
| C. Data Quality Status* | | | | |
| 8. Coding Alert | | | | |
| 8.10 Ungroupable Data: MCE** | 0 | 0.0 | 0 | 0.0 |
| 8.9 Invalid Codes: MCE | 0 | 0.0 | 0 | 0.0 |
| 8.8 Invalid Codes: Other Edits | 3 | 1.4 | 5 | 2.3 |
| 8.7 Code-Demographic Conflict: MCE | 0 | 0.0 | 0 | 0.0 |
| 8.6 Missing Required Codes: MCE | 0 | 0.0 | 0 | 0.0 |
| 8.5 Term Selection: MCE | 3 | 1.4 | 7 | 3.2 |
| 8.4 Code Choice: MCE | 0 | 0.0 | 1 | 0.5 |
| 8.3 Code-Code Inconsistency: MCE | 0 | 0.0 | 0 | 0.0 |
| 8.2 Code-Code Inconsistency: Other Edits | 26 | 12.0 | 44 | 20.4 |
| 8.1 Code Sequencing: MCE | 0 | 0.0 | 0 | 0.0 |
| Total | 32 | 14.8 | 57 | 26.4 |
| 7. PRO Alert | | | | |
| 7.11 Elective Px Precerts | 27 | 12.5 | 48 | 22.2 |
| 7.10 Px Not Covered by Medicare | 0 | 0.0 | 0 | 0.0 |
| 7.9 Questionable Medicare Coverage: MCE | 0 | 0.0 | 0 | 0.0 |
| 7.8 Questionable Medicare Coverage: Oth | 0 | 0.0 | 0 | 0.0 |
| 7.7 Symptom/Sign as Dx1 | 0 | 0.0 | 15 | 6.9 |
| 7.6 Acute Version of Chronic as Dx1 | 0 | 0.0 | 0 | 0.0 |
| 7.5 Other Codes Inappropriate as Dx1 | 0 | 0.0 | 0 | 0.0 |
| 7.4 Other Questionable Case Reporting | 4 | 1.9 | 20 | 9.3 |
| 7.3 DRG 468 (intensification) | 0 | 0.0 | 0 | 0.0 |
| 7.2 DRG 475 (vent. support) | 1 | 0.5 | 1 | 0.5 |
| 7.1 Special Study: | 0 | 0.0 | 2 | 0.9 |
| AIDS Coding TOTAL | 32 | 14.8 | 86 | 39.8 |
| 6. Resources Utilization? | | | | |
| 6.3 Admission Medically Necessary? MCE | 0 | 0.0 | 0 | 0.0 |
| 6.2 Admission Medically Necessary? Other | 0 | 0.0 | 0 | 0.0 |
| 6.1 Procedure Medically | 26 | 12.0 | 61 | 28.2 |

TABLE 3-continued

MAXIMONITOR PRE-REVIEW DIAGNOSTIC PROFILE
(Priority sequenced for selecting review cases)

Hospital: OPRS TEST RUN - 8/22/91
Payor: All   Date Range:
Base Rate: 1000   Grouper Used: 8.0

|  | # | Maximized Cases % of Tot | # | Total Cases % of Tot |
|---|---|---|---|---|
| Necessary? |  |  |  |  |
| TOTAL | 26 | 12.0 | 61 | 28.2 |
| 5. Documentation Deficient? | 0 | 0.0 | 0 | 0.0 |
| TOTAL | 0 | 0.0 | 0 | 0.0 |
| 4. Substantiating Data? | 0 | 0.0 | 0 | 0.0 |
| TOTAL | 0 | 0.0 | 0 | 0.0 |
| 3. Incomplete Abstract? | 0 | 0.0 | 0 | 0.0 |
| TOTAL | 0 | 0.0 | 0 | 0.0 |
| 2. Veracity Cases |  |  |  |  |
| 2.4 Questionable Clinical Status | 1 | 0.5 | 9 | 4.2 |
| 2.3 Questionable Clinical Management | 0 | 0.0 | 0 | 0.0 |
| 2.2 Unreported CC? | 0 | 0.0 | 0 | 0.0 |
| 2.1 Other Potential Underreporting | 0 | 0.0 | 1 | 0.5 |
| TOTAL | 1 | 0.5 | 10 | 4.6 |

D. Veracity Ratio:

| Total Veracity Messages | Total Messages | Veracity Ratio |
|---|---|---|
| 167 | 535 | 0.3121 |

*Note: Problem cases are assigned to only one data quality status category and are ranked sequentially from the highest to lowest priority. Any case with multiple data quality messages will be counted only one in the highest ranked priority category.
**MCE = Medicare Edits

TABLE 4

Report date: 12/20/90
QUICKSCREEN CASE REVIEW LIST
 FINANCIAL RISK CASES 
MEDICAL CENTER Class 13 Cases (Coding Alert - Financial)

| Patient ID | DOB | DOA | DOD |
|---|---|---|---|
| 00216787010 | 05/05/25 | 12/04/90 | 12/18/90 |

| # Cases | % Sample |
|---|---|
| 1 | 3.1 |

Class 11 Cases (Incomplete Abstract? - Financial)

| Patient ID | DOB | DOA | DOD |
|---|---|---|---|
| 00010187005 | 04/02/23 | 12/04/90 | 12/18/90 |
| 00085446035 | 08/01/26 | 12/07/90 | 12/13/90 |
| 00097680023 | 12/16/11 | 12/01/90 | 12/13/90 |
| 00174167017 | 01/16/20 | 12/15/90 | 12/18/90 |
| 00401189001 | 03/26/23 | 12/13/90 | 12/18/90 |

| # Cases | % Sample |
|---|---|
| 5 | 15.6 |

Class 9 Cases (Documentation Request - Financial)

| Patient ID | DOB | DOA | DOD |
|---|---|---|---|
| 00001846017 | 08/18/05 | 11/29/90 | 12/17/90 |
| 00029166029 | 10/31/58 | 12/02/90 | 12/17/90 |
| 00092680016 | 11/18/16 | 12/06/90 | 12/13/90 |
| 00092680017 | 11/18/16 | 12/17/90 | 12/18/80 |
| 00378209994 | 02/23/25 | 12/10/90 | 12/14/90 |
| 00380802004 | 09/19/09 | 11/26/90 | 12/14/90 |
| 00400103001 | 08/30/25 | 11/29/90 | 12/18/90 |
| 00400179001 | 03/07/10 | 11/30/90 | 12/12/90 |

| # Cases | % Sample |
|---|---|
| 8 | 25.0 |

Class 7 Cases (Substantiating Data? - Financial)

| Patient ID | DOB | DOA | DOD |
|---|---|---|---|
| 00008182015 | 06/15/19 | 12/13/90 | 12/14/90 |
| 00178984013 | 05/22/09 | 12/10/90 | 12/18/90 |

TABLE 5

QUICKSCREEN HOSPITAL RECORD PULL SHEET
 FINANCIAL RISK CASES 
MEDICAL CENTER

| Patient ID | Patient Name | DOB | DOA | DOD |
|---|---|---|---|---|
| 00001846017 | _____ HELEN A | 08/18/05 | 11/29/90 | 12/17/90 |
| 00008182015 | _____ , HELEN M | 06/15/19 | 12/13/90 | 12/14/90 |
| 00010187005 | _____ , PATRICIA C | 04/02/23 | 12/04/90 | 12/18/90 |
| 00029166029 | _____ , WAYNE S | 10/31/58 | 12/02/90 | 12/17/90 |
| 00085446035 | _____ , ANNIE R | 08/01/26 | 12/07/90 | 12/13/90 |
| 00092680016 | _____ , ANNA M | 11/18/16 | 12/06/90 | 12/13/90 |
| 00092680017 | _____ , ANNA M | 11/18/16 | 12/17/90 | 12/18/90 |
| 00097680023 | _____ , ANNABELLE E | 12/16/11 | 12/01/90 | 12/13/90 |
| 00174167017 | _____ , DERWOOD E | 01/16/20 | 12/15/90 | 12/18/90 |
| 00178984013 | _____ , HARM | 05/22/09 | 12/10/90 | 12/18/90 |
| 00204716028 | _____ , KENNETH H | 06/28/31 | 12/14/90 | 12/15/90 |
| 00216787010 | _____ , MARIE | 05/05/25 | 12/04/90 | 12/18/90 |
| 00273887015 | _____ , JOSEPH D | 08/06/47 | 12/08/90 | 12/15/90 |
| 00300044013 | _____ , HAZEL M | 04/11/21 | 12/14/90 | 12/18/90 |
| 00339457005 | _____ , STANLEY E | 03/26/13 | 12/12/90 | 12/15/90 |
| 00378209004 | _____ , PERCY C | 02/03/25 | 12/10/90 | 12/14/90 |
| 00380802004 | _____ , DORIS | 09/19/09 | 11/12/90 | 12/14/90 |
| 00400103001 | _____ , JUANITA | 08/30/25 | 11/29/90 | 12/18/90 |
| 00400179001 | _____ , ELMER L | 03/07/10 | 11/30/90 | 12/12/90 |
| 00401189001 | _____ , MARIA | 03/26/23 | 12/13/90 | 12/18/90 |

Total Cases on Report: 20 (End of Report)

TABLE 6

Date report printed: 03/03/88
Hospital
Revenue Impact Report: Summary of Differences between
Initial and Final DRG Assignments
Discharge data range: 01/01/88 thru 01/31/88

| PAYER | CASES # | # | AVG % | CHNG/CASE COST WEIGHT DOLLARS | TOTAL CHGN ALL CASES COST WT DOLLARS | EXPECTED PMT/CASE COST WT DOLLARS | TOTAL EXPECTED PAYMENT COST WT DOLLARS |
|---|---|---|---|---|---|---|---|
| 1 | 442 | 36 | 8% | 0.0287 | 12.6999 | 1.6902 | 747. |
| Rate 4292.00 | | | | 123.32 | 54508. | 7254. | 3206389. |
| 2 | 148 | 6 | 4% | −0.0015 | −0.2233 | 0.9965 | 147. |
| Rate 1000.00 | | | | −1.51 | −223. | 996. | 147479. |
| 3 | 4 | 0 | 0% | 0.0000 | 0.0000 | 0.7350 | 3. |
| Rate 1000.00 | | | | 0.00 | 0. | 735. | 2940. |
| 4 | 292 | 15 | 5% | 0.0232 | 6.7727 | 1.1263 | 329. |
| Rate 1000.00 | | | | 23.19 | 6773. | 1126. | 328875. |
| 5 | 17 | 2 | 12% | 0.0367 | 0.6235 | 0.7661 | 13. |
| Rate 1000.00 | | | | 36.68 | 624. | 766. | 13024. |
| 6 | 0 | 0 | 0% | 0.0000 | 0.0000 | 0.0000 | 0. |
| Rate 1000.00 | | | | 0.00 | 0. | 0. | 0. |
| 7 | 0 | 0 | 0% | 0.0000 | 0.0000 | 0.0000 | 0. |
| Rate 1000.00 | | | | 0.00 | 0. | 0. | 0. |
| 8 | 0 | 0 | 0% | 0.0000 | 0.0000 | 0.0000 | 0. |
| Rate 1000.00 | | | | 0.00 | 0. | 0. | 0. |
| 9 | 48 | 3 | 6% | 0.0231 | 1.1111 | 0.9468 | 45. |
| Rate 1000.00 | | | | 23.15 | 1111. | 947. | 45446. |
| ??UNKNOWN | 0 | 0 | 0% | 0.0000 | 0.0000 | 0.0000 | 0. |
| Rate 1000.0− | | | | 0.00 | 0. | 0. | 0. |
| Total | 951 | 62 | 7% | 0.0221 | 20.9840 | 1.3510 | 1285. |
| | | | | 66.03 | 62792. | 3937. | 3744152. |

ORG 470 excluded

TABLE 7

HOSPITAL [ / ]
SYSTEM ACTIVITY REPORT: MESSAGES AND WORKSHEET
GENERATED
Discharge Months: 11/01/90–11/30/90

Section I MESSAGES 7 WORKSHEETS GENERATED

| Worksheets | Total Cases # | Cases w/o msgs # | Cases w/o msgs % | Cases w msgs # | Cases w msgs % | Worksheets Sent # | Worksheets Sent % | Worksheets Voided # | Worksheets Voided % | Worksheets/c w/o msg # | Worksheets/c w msg # |
|---|---|---|---|---|---|---|---|---|---|---|---|
| MRD | 1 | 0 | — | 1 | 100 | | | | 100 | 2.0 | — |
| Physician | 57 | 1 | 2 | 56 | 98 | 33 | 58 | 17 | 30 | 1.0 | 1.3 |
| Attestation | 0 | 0 | — | 0 | — | | | 0 | — | — | — |
| No wrkshts | 19 | 0 | — | 19 | 100 | | | | | | |
| Total | 77 | 1 | | 76 | | | | | | 3.0 | 1.3 |

Section II TYPES OF MESSAGES

| | | Initial Messages # |
|---|---|---|
| 1. | Coding Problems | |
| | 1.1 Unreported Data | 0 |
| | 1.2 Invalid Code(s) | 4 |
| | 1.3 Code-Demographic Conflict | 3 |
| | 1.4 Missing Required Code(s) | 9 |
| | 1.5 Term. Selection | 17 |
| | 1.6 Code Choice | 8 |
| | 1.7 Code-Code Inconsistency | 31 |
| | 1.8 Code Sequencing | 4 |
| 2. | Documentation Questions | |
| | 2.1 Unrecorded Med Judgment | 9 |
| | 2.2 Missing Required Doc | 36 |
| 3. | Abstracting Issues | |
| | 3.1 Incomplete DX Desc? | 0 |
| | 3.2 Incomplete PX Desc? | 0 |
| 4. | Data Substantiation Issues | |
| | 4.1 Substantiation for Dx1 | 29 |
| | 4.2 Other Clinical Sub. | 0 |
| 5. | Underreporting | |
| | 5.1 Unreported Missing Dx(s) | 0 |
| | 5.2 Unreported Dx Specificity | 0 |
| | 5.3 Unreported Procedure | 0 |
| | 5.4 Unreported-unspec Px(s) | 0 |
| 6. | Utilization Questions | |
| | 6.1 DxServices Appropriate? | 0 |

TABLE 7-continued

HOSPITAL [ / ]
SYSTEM ACTIVITY REPORT: MESSAGES AND WORKSHEET
GENERATED
Discharge Months: 11/01/90-11/30/90

|   | 6.2 Theraputic Svc Approp | 0 |
|---|---|---|
| 7. | Rule Change Reminders |   |

Section III AVERAGE PROCESSING TIMES

|   | days |
|---|---|
| Discharge to record received | — |
| Record received to first ATT document gen | — |
| ATT document generated to signature | — |
| Case closure to archive | 43.4 |

(1) Messages initially present, and not resolved by subsequent data quality improvement(s)

TABLE 8

DATA QUALITY IMPROVEMENTS
AND ASSOCIATED REVENUE IMPACT
PAYOR (01): Medicare
Base Rate Used $ .00
Discharge Months: 11/01/87-11/30/87

Section I CHANGES IN DRG ASSIGNMENTS

|   | Hospital | |
|---|---|---|
|   | # | % |
| Cases with DRG Change | 49 | 9 |
| Cases w/o DRG change | 482 | 91 |
| Total Cases | 531 | 100 |

Section II RESOLVED MESSAGES ASSOCIATED WITH CHANGES (1)

| | Realtive Cases | | Frequency Cases | | Relative Revenue Impact | |
|---|---|---|---|---|---|---|
| TYPES | w Data Changes | | w DRG (2) Changes | | Avg. Chng Per | Total Change |
| OF MESSAGE | # | % | # | % | Case $ | $ |
| Documentation | | | | | | |
| 1. Term Selection | 241 | 45 | 22 | 45 | 100. | 53321. |
| 2. Sequencing | 165 | 31 | 15 | 31 | 48. | 25454. |
| 3. DRG Reminders | 121 | 23 | 13 | 27 | 56. | 29921. |
| Sub Total | 527 | 99 | 49 | 100 | 205. | 108696. |
| Coding & Reporting | | | | | | |
| 4. Code Choice | 4 | 1 | 0 | 0 | 0. | 0. |
| 5. Missing Required Code | 0 | 0 | 0 | 0 | 0. | 0. |
| Sub Total | 4 | 1 | 0 | 0 | 0. | 0. |
| Grand Total | 531 | 100 | 49 | 100 | 205. | 108696. |

(1) Resolved messages are those that were initially present, but were later resolved by subsequent data quality improvements. Due to potential double-counting when multiple messages are resolved per case, all entries have been proportionally adjusted to sum up the actual grand totals.
(2) Since not all data changes result in DRG changes, figures in this column are lower than the data change column.

A BRIEF DESCRIPTION OF THE PROCESS DIAGRAM OF FIGS. 2a AND 2b

Block 76, Enter Patient Data

Data are entered into the patient database 12 manually or, more commonly, in a batch operation via a download from another computer environment. Patient identifier and demographic information are entered first. Clinical data (diagnosis and procedure codes) may be entered immediately or at a later time depending upon the type of record review and coding process being conducted. Data entry is done "concurrently" for presently-hospitalized patients. It is done "retrospectively" for patients already discharged. A system option located in the utility program allows the user to preset the type of data entry mode. When set to the retrospective data entry mode, certain data fields require mandatory entries that, in the concurrent mode, are allowed to be incomplete, such as the hospital discharge date. Another requirement that must also be accommodated for the concurrent operating mode is the temporary insertion of a dummy discharge date (i.e. year) in order to select and operate the appropriate DRG grouper program.

The criteria for determining data field completeness are controlled by the user's selection of concurrent versus retrospective data entry modes in the utility program 14.

General Data Edits

Basic data edits are performed in real time upon input in order to assess the following:
Data field validity,
Coherency of dates,
Data base consistency,
Completeness of the data set.

Inconsistent, non-coherent, and otherwise invalid data are not permitted entry into the patient database. A record is made of all cases with invalid data. If cases with invalid data were encountered through a download operation, a data error summary and an itemized listing of all cases with errors are printed automatically.

Block 78, Check and Classify Each Case

Once all the clinical data have been entered, they are subjected to additional sets of edits.

Use of Data Quality Edits: These content-oriented edits can be applied only to technically valid data. Their purpose is to determine whether the clinical information conveyed via diagnosis and procedure codes is adequate to describe case complexity and is consistent with both coding rules and established data reporting rules. These edits are designed to assess:
Actual violations of coding or reporting rules
Potential violations of coding or reporting rules
Consistency with optimal reporting practices
Questionable medical (i.e. diagnostic) indications for services
Questionable utilization of medical resources (See Table 2 for a full listing of data quality edits.)

Patient data, consisting of diagnosis and procedure codes plus certain personal attributes such as age and gender, are processed through a series of data check subroutines designed to assess the quality of the reported data. The automated data review program (see block 26) compares data entries to trigger files and tables (see block 22) that identify actual and potential error conditions and suboptimal case descriptions.

Message classification: Once the error conditions are identified, corresponding data quality messages are generated from text files. Once generated, the messages are then classified according to type by referencing them to the Message Class Definition Table (see block 16).

All messages generated for all cases are classified in an hierarchical manner based upon the importance of their content. The more serious the reporting error or data quality problem, the higher the hierarchical class assignment. A record of the messages generated and their classifications is stored in the Edit Results File 30.

Identification of review cases: Once all messages have been classified hierarchically on the basis of their content, the next processing step is to employ this classification to identify which cases should qualify as "review cases" and therefore merit record-based review and further processing steps.

The user defines the criteria by which cases are selected for review by using the system utility (see block 14). The user selects which hierarchical class and/or subclasses of messages are to trigger the printing of review documents at block 80 (i.e. worksheets). The user's priority selections are stored in Review Case Definition table(s) (see block 18). Messages generated during the Automated Data Review program (see block 26) are then checked against the user's selections. When there is a match between the classifications of messages generated by the given case and the review definition, the case is defined as a "review case." Another Review Case Definition table may also be employed to segregate cases on the basis of some other classification or type of messages they contain.

Processing of non-review cases: For those cases that fail to meet the definition of a review case, no further processing is necessary other than to issue a confirmatory notice of this fact on a feedback report. Depending on user needs, this notification may take the form of a printed listing of non-review cases, a printed attestation document to elicit confirmation of data entries by the attending physician, or an appropriate frequency count entered onto a Data Quality Profile Report 36. Through option selections made in the system utility program 14, the user may elect to implement all three transactions cited above.

For cases that do meet the definition of a review case, the additional processing steps described below will occur in order to support human case review activities.

Generation of worksheets (block 28): Case review worksheets designed to function as turn-around documents are generated according to user options that have been preset in the system utility program 14. The content of worksheets includes case identification information, error and data quality messages that identify problems detected in data quality. Through reference to another Review Case Definition table 18, messages are selectively addressed to nurses or review coordinators, coders, and physicians, i.e. messages are routed to the appropriate user-oriented worksheets.

Use of DRG Grouper: A translated version of the Federal Government's DRG grouper program is frequently called as a subroutine throughout the data checking process (see block 20). The Grouper is used to assign the appropriate Diagnosis Related Group (DRG) upon which hospital payment is based. It is also used to assess the role that various data elements play in arriving at a DRG assignment.

Calculation of Maximization of Payment: Maximization of payment resulting from the data reporting sequence of diagnosis codes involved in assigning DRGs is also determined for each case as part of the data checking process. See Table 3 for description of maximization algorithm. These calculations will be stored for later use in generating data summary reports (see block 36, block 134, block 48 and block 174). The type of worksheet(s) to be generated is selected before the data checks are performed in a batch operation.

Block 82, Print Lists of Initial Summary Report

Initial Data Profile Report 88: This report contains percentages and counts of cases in each hierarchical category of data quality messages. In the event a case generates multiple messages, a given case is assigned to the category of the message with the highest priority, i.e. in an hierarchical order. The frequency and distribution of messages characterize the quality of the initial data, i.e. prior to implementing data correction procedures. The Initial Profile Report also includes percentages and numbers of cases with diagnoses and/or procedure codes that have been sequenced to achieve maximum DRG-based payments. A Veracity Index may also be displayed which is a surrogate measure of honesty in reporting.

Case Review List 84: Cases are classified on the basis of highest priority of their message content (also referred to as "data quality status"). Typically, this list is used to assign cases to review personnel who possess the professional expertise required to respond to them.

Hospital Record Pull List 86: Case identification information is listed for all review cases that have been selected by user criteria. Typically, this list is used to retrieve the hospital records for a grouping of the review cases.

Block 90, Analysis of "Review Cases"

Review personnel typically are medical record specialists and/or nursing personnel who are backed up by attending physicians or physician advisors, depending upon the environment in which the analysis of medical records takes place. The review of medical records is directed by data quality messages contained on worksheets oriented to the primary review personnel. Worksheets that contain messages or requests for clarification that entail the exercise of medical judgment may be transmitted to the responsible attending physician (or to a physician advisor) on printed paper forms called physician worksheets. Similarly, messages that address coding issues are printed on coding worksheets and routed to data specialists.

Block 92, Correction of Clinical Data

Data corrections are entered into the patient database 12 either manually, i.e. interactively, or by batch mode via a download program 74.

Revisions in clinical data that result in new DRG assignments also result in revised payment-related information which is subsequently recalculated and stored for use in preparing final summary reports 94.

Block 94, Print Final Summary Reports

The final Data Profile Report 96 is printed after a batch of cases has been reviewed and all relevant corrections are made to the data set. The format of this report is essentially identical to that of the initial Data Profile Report 36. Its content, however, characterizes the quality status achieved after data corrections have been made. For purposes of comparison, data quality status figures for the initial data may be displayed along side the final data quality status results. Cases can be selected for inclusion in this report by date range.

A DRG-change or "Revenue Impact" Report 98 can also be generated from corrected data. This report is comprised of two parts: a case-by-case list of changes in DRG assignments and associated payment rates, and an overall summary of the financial impact on hospital payments of data corrections introduced through the entire review process.

Block 100, Data Archival Program (also see block 52)

The data archival program is an integrated series of automated processes initiated periodically to achieve the following objectives:
1). systematically remove closed (i.e. completed) cases from the active patient data base,
2). generate a cumulative body of patient data, performance data, and payment data from which a variety of data quality, financial impact, and management reports can be created,
3). store historical data in a machine-retrievable form in the event that contingent data recall later becomes necessary.

This archival process is unique in that data of many differing types are stored together in specific configurations designed to facilitate the generation of a wide variety of useful summary reports. Not only are the more obvious data elements stored together in readily accessible files (such as patient demographic information along with diagnoses and procedures and hospital stay data) these archive volumes also store in a mix of other types of information such as data quality status assessments, financial impact data, historical records of data processing activities, and personnel performance data. Further description of the Data Archival Program is provided in Systems Diagram blocks 54 and 56.

The Archival Patients Records File (see block 54) contains configuration of data from which a variety of financial reports 102 are efficiently generated. Two types of Revenue Impact Reports 104 are generated from cumulative case data that quantify the extent to which the data correction process has altered hospital payments. One of these reports documents the measurable impact of a retrospective data correction process and another report of differing content and format documents the measurable impact of a concurrent data correction process.

An optional companion to either type of summary report is a detailed case listing which provides side-by-side companions of DRG assignments and resultant payments for each case based upon initial versus final patient data. Other financial reports that can be generated from this archive file includes DRG distribution (i.e. case mix) reports and message frequency distribution reports.

The Data Quality Audit File (see block 56) contains a configuration of data from which a family of data quality reports 106 are efficiently generated. A System Activity Report 108 quantifies the amount and major types of transactional activities that have taken place during the report period and displays the impact of these activities on the quality and accuracy of the claims data. Also displayed are averaged time frames required to complete various phases of the data correction process.

Medical Specialty Reports 110 consist of more targeted versions of the System Activity Report that focuses on the performance of physicians in the data correction process. These reports may aggregate physician performance data by medical specialty in order to detect systematic error in claims reporting as a function of medical or surgical subspeciality orientation.

Similar reports can also be generated to characterize claims reporting patterns by individual physicians. Reports of this kind typically are used to tailor appropriate educational interventions. Coder reports 112 focus on the performance patterns and coding proficiency displayed for groups of data specialists or by individual coders. Reports of this kind are primarily used in the supervision of data specialists.

Data Quality Improvement Reports 114 are higher level management reports that characterize the overall performance of all personnel involved in the data correction process. Reports of this kind are especially valuable when repeated at appropriate time intervals in order to detect trends in the efficiency and effectiveness of data correction activities.

The preceding SYSTEM and PROCESS DIAGRAMS describe the fundamental components and the operational sequences of the basic Patient Data Quality Review Program. These fundamental components and processes will next be described in two different functional configurations that result in the creation of two differing application products designed for operational use in entirely different environments. Where appropriate, cross-references will indicate which specific system and process blocks are required to perform the functions described in the FUNCTIONAL DIAGRAMS. The first of these two Functional Diagrams describes the configuration of the basic Patient Data Quality Review System that is appropriate for application in hospital environments.

A GENERAL DESCRIPTION OF THE FUNCTIONAL DIAGRAM FOR HOSPITAL-BASED APPLICATIONS OF FIG. 3

The Hospital-based configuration of the Patient Data Quality Review System is defined as a combination of batch-operated and interactive computer software programs designed to increase the effectiveness and efficiency of data quality control operations in the preparation of DRG-based hospital claims.

Explanation of Functional Diagram

The hospital-based application of the case processing system consists of a series of discrete functions that can be divided into two distinctly different phases (see notations on left side of Functional Diagram). In phase I, many manual functions ordinarily associated with the process of screening hospital claims data for the presence of reporting errors are replaced with fully automated functions. Phase II of the data correction process consists of computer-assisted, interactive case review and data correction functions that, by legal mandate, require human input.

Appearing below is a brief description of the major operational functions performed in hospital-based applications of both phases of the data correction process.

PHASE I. BATCH PROCESS (AUTOMATED SEQUENCE OF STEPS)

Block 116, Data Set Entered

The function of entering hospital claims data can be accomplished either by the standard key entry of individual cases (i.e. as a clerical function) or more typically by a batch download from another computer (see block 72). Essential data elements include patient identifiers, demographic data, and ICD-9-CM codes for all relevant diagnoses and O.R. procedures. While case data are in the process of being entered or downloaded, they are continually checked for completeness and data field validity (see block 74). Cases with incomplete or invalid data are identified for follow-up investigation but are not permitted to enter the patient database for further processing.

The next seven major operations are all performed jointly through batch operations upon the entire group of cases entered into the patient data base. All these batch operations are performed by an independent computer program. However, patient data are stored in a file that can later be retrieved for correcting and updating claims data interactively (block 42).

Block 118, Bach Data Quality Checks

Data quality checks covering a broad spectrum of reporting rules and requirements (see block 26) are performed on all cases selected from the patient database (see block 12) for the given batch run. Once the data quality edits are performed the next step is to determine whether the data for each case contain actual errors or potential data quality problems as defined by established rules for the reporting of hospital claims data. On the basis of what types of messages they do or do not generate (see block 16), cases are next passed through what amounts to a filtering operation.

All cases are fed from one batch operation to the next (see block 76 through block 82) until a set of worksheets containing case-generated messages is produced to guide a focused review of the medical record by appropriate personnel.

The classification of messages is a necessary preparatory step of prioritizing review efforts in the hospital environment. Specifically, messages are first passed through a Message Class Definition Table (see block 16) that labels problems in data quality as to their probable cause. This orientation aids the hospital personnel in understanding the best approach to correcting the data.

The messages are then passed through the Review Case Definition Table (see block 18) that sorts problems in data quality into the types of risks to which the hospital is exposed should the problem(s) in data quality detected for a given case. More specifically, each data quality message is labeled as to whether it exposes the hospital to a potential risk of invoking a penalty for the misreporting of claims data or a risk or inappropriate underpayment.

From a functional viewpoint, the first classification step (block 12) "filters" (i.e. sorts messages as to their causation whereas the second classification step (block 128) filters them according to their relative importance (i.e. priority for subsequent corrective action).

Block 120, Problem Case Filter

In passing through this second "filtering" operation (see block 128), all cases in the group being screened are functionally segregated into one of three separate data streams depending upon whether any data quality messages were generated and, if so, of what type.

Cases that generated no data quality messages are considered complete and may be passed on immediately to the billing operation. On the flow diagram, these cases are channeled into Data Stream A. Note also that cases that generate only messages that are of low priority in block 128, i.e. those that do not meet the user's definition of a review case, are also channeled to block 122 through Data Stream C-1.)

Cases with messages that typically are associated with inappropriate underpayments to the hospital (i.e. "potential financial loss" cases) are channeled into Data Stream B.

Channeled into Data Stream C are cases of the type that could trigger a review by the Peer Review Organization (PRO), cases that fail Medicare edit checks, and cases that generate messages indicating some other potential for being misreported. Cases of this type expose the hospital to possible penalties.

Block 122, Forward to Billing (Data Stream A)

Cases in the first data stream, i.e. those that generated either no data quality messages or messages of low priority, are immediately made available to the billing process. Depending upon the data transfer option chosen, these cases can be passed directly to main-frame billing operations automatically via a batch upload to the mainframe computer (see block 74). Alternatively, a special billing interface document, also prepared in a batch process, can be generated for inputting data from each case into the billing operation.

Block 124, Batch Printing and Logging Of Worksheets (Data Stream B)

Worksheets of a pre-selected type are printed and logged in a batch operation (see block 26) for all cases generating data quality messages that indicate a risk of inappropriate underpayment to the hospital. At least one of the messages printed on worksheets generated from Data Stream B must be associated with a significant potential for financial loss to the hospital to qualify a case for this data stream. Simultaneously, as those worksheets are produced, they are automatically logged by the system for later tracking through the entire data correction process. Worksheets may be logged-out to different review teams or even individuals depending on the type of expertise most appropriate to respond to different classes of messages.

A case assignment listing, also generated automatically, is produced to facilitate the logistics of managing the review of all cases in the group. The user may opt not to print worksheets for certain classes of messages and instead display them on the screen in support of interactive case review activities such as concurrent coding operations (see block 96 or block 92).

Block 126, Worksheets Generated for Cases With Potential Financial Loss (Data Stream B)

Worksheets generated from Data Stream B may contain a variety of individual messages but, in general, they pertain to understatements of case complexity resulting from the use of inappropriate or non-specific diagnostic or procedure terms, unexercised or unstated clinical judgments and/or inadequate record documentation. What these cases have in common as a group is a significant potential for incurring unnecessary underpayments to the hospital because of a failure on the part of the attending physician to report or substantiate diagnoses or procedures that fully describe case complexity. The objective in reviewing these cases is to determine whether legitimate reporting options exist that more accurately reflect case complexity, whether the cass are in compliance with existing reporting rules and whether any of these cases should be referred to the appropriate physician for this purpose.

Personnel most qualified to perform the initial review of cases of this type are those with in-depth knowledge of medical terminology and clinical reporting requirements. Clinical data specialists such as utilization review or quality assurance nurses determine whether it is appropriate to refer on to the responsible physician some selected messages that pertain to record documentation or medical judgment issues that only the physician can resolve.

Block 128, Prioritize Cases for Review (Data Stream C)

Segregated into Data Stream C by the problem case "filter" transaction are those cases with a relatively low potential for inappropriate financial loss to the hospital but that exhibit a significant potential to invoke penalties for misreporting. There is considerable variance among cases of this kind with regard to their seriousness, i.e. the potential consequences of misreporting. Accordingly, the capability has been added to enable the user to prioritize such cases for in-depth review. As depicted in the functional diagram, this capability has been inserted into Data Stream C as a second "filter" operation.

The process leading up to the setting of these priorities is described briefly as follows:

- A suitable data base of several hundred cases is first accumulated for the purpose of serving as a baseline. The quality of the data, exhibited by what preferably is a representative sample of actual cases, is then analyzed.
- A data quality report is next generated that categorizes the types of misreporting detected within the given sample of cases. These categories (and subcategories) of data quality messages are ranked according to their seriousness or potential consequences, e.g., are grouped on the report as to whether a mandatory external review has been triggered or whether the cases have failed Medicare edits and consequently could result in the suspension of payment, etc. Where appropriate, cases are also ranked as to whether the generated messages pertain to "actual reporting errors," or "potential reporting problems," etc.
- With previous system performance data as a guide and taking into account the availability of personnel, the user then sets the option switches that pre-select which categories of cases will receive sufficiently high priority to qualify for the in-depth review process of Data Stream C-2 and which cases are considered sufficiently low in priority that they will be automatically passed on to the billing operation (Data Stream C-1).
- The selection switches that prioritize these cases for in-depth review are located in the system utility program (see block 14). These switches are easily re-set, and this may be done at any time.

Block 130, Batch Printing And Logging Of Worksheets (Data Stream C-2)

This mechanical operation is virtually the same as that described under block 124 with only one difference. The operator may pre-select a different type of worksheet to be generated and logged for cases in Data Stream C-2 than were generated in Data Steam B. The ability to choose alternative types of worksheets is desirable if various classes of messages are to be reviewed by personnel with different professional orientations.

Block 132, Worksheets Generated for Cases With Potential Misreporting (Data Stream C-2)

Worksheets generated from Data Stream C-2 pertain largely to the technical aspects of claims reporting that will, or are likely to, expose the hospital to penalties. Some classes of messages arise from non-compliance with coding rules or reporting requirements, so that coders would be the most appropriate initial reviewers of these cases. However, some messages for cases in this data stream arise from ambiguities or deficiencies in documentation on the medical record. Hence, many of the messages generated by cases in Data Stream C-2 are more clinical in their orientation than those typically found in Data Stream B. Personnel qualified to perform the initial review of cases of this kind would include experienced coders.

In the event the user does wish to employ different individuals or review teams for responding to cases with clinically-oriented messages than those normally employed to respond to messages related to coding rules and reporting requirements, the system can be pre-set to determine which type of worksheets will be generated for which person or team. The system can then separately track worksheets produced for the different personnel or teams.

Block 134, Initial Profile Report and Case Listings

The Initial Data Profile report set referred to by block 36 of the System Diagram is normally printed out at this time and used as an administrative tool to help manage the data correction process. One of the reports in this set summarizes the quality of the claims data processed in data streams B and C-2, i.e. potential financial loss cases and high priority potential penalty cases. Taken together, the distribution of cases in these problem categories define the nature and amount of work that will be required to correct the data. This is information useful for assessing overall work requirements.

Specific problems in data quality are identified by individual case in listings that accompany the summary report. One list identifies cases according to the most serious type (classification) of problems in data quality that it presents. Problem classifications at this level correlate with the type of expertise required to resolve them. This type of listing is useful in assigning review cases to personnel who possess the expertise needed.

Other case listings are generated as management tools to enhance efficiency and assure completeness of the review process.

As depicted in the flow diagram, the Initial Profile Report and the case listings typically are generated before an automatic generation of worksheets occurs. This is the usual operational mode. In an alternative scenario, worksheet generation can be made contingent or responsive to findings in the Initial Profile Report. In short, a human decision can be interposed on a daily basis as to which classes or subclasses of data quality problems will be defined as review cases. That decision, in turn, will determine the cases for which worksheets will be generated.

To facilitate the management task of supervising case review teams, separate case assignment listings can be used to prioritize the review activities for each data stream (see block 82).

PHASE II. INTERACTIVE PROCESS

Block 136, Record-Based Case Review (Data Stream B & C-2)

Worksheets of a pre-selected type and containing only messages appropriate to the professional expertise of the recipient are utilized in conducting record-based case review. For example, Coding Worksheets containing only messages relating to coding issues are routed to coding specialists for their responsive action. Similarly, worksheets containing clinically oriented messages are routed to clinical personnel.

In the course of the initial case review, a decision is made concerning the case relevance of each message. If found to be relevant on the basis of existing documentation in the medical record, the next decision is whether the data elements questioned were actually misreported or not. If found to be misreported, a determination is made whether sufficient information has been documented on the medical record to substantiate a correction of the data.

If adequate substantiating documentation already exists on the medical record, the initial reviewer corrects the data (usually involving the correction or resequencing of diagnosis or procedure codes).

Block 138, Enter Corrections for Each Case

Upon completing a review of the medical record directed by the data quality messages, any corrections or additions to the data that are appropriate can be made by using the update transactions of the hospital-based Patient Data Quality Review System. All logging and tracking operations are fully functional to assist data handling for every case in all data streams. Case assignment lists can also be generated to track the review process for separate review teams or individuals.

Block 140, Forward To Billing

As in block 122, completed cases can be forwarded to billing operations (by) either of two data streams previously described (streams B and C).

A special feature built into the data upload option (see block 54) makes it possible to implement decisions concerning which cases to upload (and when) under full optional control. Not only does this facilitate case closure, but it also insures integrity of the database and further speeds up the billing process.

Block 142, Final Profile Report and Case Listings

After all data corrections have been made for a group of cases, a second data quality profile report is generated to document the extent to which the quality of patient data has been improved. Typically, such reports are processed monthly or quarterly from archived data in order to monitor the overall performance of the data correction process and performance trends over time. Case listings categorized by the type of data quality problems found typically are used for more detailed, i.e. case-specific quality control surveillance of the data correction process.

As with the Initial Profile Report and case listings (blocks 36 and 38), there is an alternative scenario for using the "final" versions of these output reports. When initial reports are generated on a daily basis, the final reports generally are also. Typically, the initial report and listings would be generated at the beginning of a working day and their final versions generated toward the end of the work day. When this usage scenario is invoked, the responsible manager can determine on the spot if the level of responses made by review personnel have been at acceptable levels of effectiveness. If it is apparent from the summary profile report that some serious problems in data quality remain unresolved, case listings may be generated to identify the specific cases involved and/or the personnel responsible to reconcile the data.

Data Archival Program

Depending upon the environment in which the system operates, it may or may not be necessary to activate the Data Archival Program in order to maintain databases or generate reports. If the data archival program is to be employed in hospital-based applications of the Data Quality Review System, it will function in the same manner as described in the Functional Diagram for third-party review applications (see block 174 and block 176).

A BRIEF DESCRIPTION OF THE FUNCTIONAL DIAGRAM FOR THIRD-PARTY APPLICATIONS OF FIG. 4

The configuration of the Patient Data Quality Review System that is designed for use by third party review applications may be defined as a combination of batch-operated and interactive computer software programs that function to enhance the effectiveness and increase the efficiency of review activities directed to assessing the accuracy of data reported on hospital claims and validating the legitimacy of DRG assignments derived from these data.

Explanation of Functional Diagram of FIG. 4

The third-party based application of the Patient Data Quality Review System is configured to perform a series of discrete functions that conceptually can be divided into two different phases. In Phase I, the preliminary case screening functions that otherwise would be performed manually by a review coordinator are performed in an automated batch operation by the program.

In Phase II, which involves human input to the case review process, many operational steps are computer-assisted, i.e. are typically performed interactively between the reviewer and the automated system. Appearing below is a brief description of the major functions performed by this system in both phases of the review process.

PHASE I BATCH PROCESS (AUTOMATED SEQUENCE OF STEPS)

Block 144, Data Set Entered

The function of entering hospital claims data into the system is typically via electronic transfer but may also be accomplished by the standard key entry of individual cases. When a download operation is being performed, the data elements are continually checked for completeness and data field validity (see block 74). Cases with incomplete or invalid data are identified but not permitted to enter the patient data base 12. Essential data elements include patient identifiers, demographic data, descriptors of the hospital stay, and ICD-9-CM codes for all relevant diagnoses and procedures. Once the patient data base is created, the data are stored in a file that can be later retrieved to support interactive review activities.

In typical installations, the next nine major operations are all performed automatically through "batch" operations on the entire group of cases entered into the patient data base 12. Because the scope of third-party review activities typically is fixed by protocol, it is possible to pre-define which cases qualify as "review cases" before the processing run is initiated. Thus, case processing can proceed in batch mode and without human intervention through block 162 which is the printing of the Initial Profile Report.

Block 146, Batch Data Quality Checks

Data quality checks covering a broad spectrum of reporting rules and requirements (see block 26) are performed on all cases selected from the patient database (see block 12) for the given batch run. Once the data quality edits are performed, the next step is to determine whether the data for each case contain actual errors or potential data quality problems as defined by establishing rules for the reporting of hospital claims data. On the basis of what types of messages are or are not generated, cases are next passed through what amounts to a filtering operation (see block 148).

The classification of messages is useful for prioritizing subsequent on-site review efforts in the hospital environment. Specifically, messages are first passed through a Message Class Definition Table (see block 148) that labels problems in data quality as to their probable cause. This aids the review personnel in understanding the best approach to correcting the data.

From a functional viewpoint, the first message classification step (see block 16) "filters" (i.e. sorts) messages as to their causation whereas the second classification step (see block 156) filters them according to their relative importance (i.e. priority) for subsequent corrective actions.

Block 148, Problem Case Filter

Passing of messages generated through the message class definition table (see block 16) classifies or labels problems in data quality as to their probable cause. In doing so, three separate data streams are created. Functionally, this step (block 148) "filters" cases into Data Stream A cases that generate no messages (i.e. have no detectable data problems). As these cases require no further review, processing is terminated, i.e. the cases are "closed" at block 150. Routed into Data Stream B are cases with potential problem involving clinical data such as incomplete diagnostic statements, those in which medical judgments are required, and those in which substantiating documentation on the medical record is in question. Cases of this kind are destined to be printed on worksheets (block 152) that re routed to physicians for review (block 154).

Cases shunted into Data Stream C are those in which a variety of actual or potential problems in data quality have been detected that are non-clinical, i.e. are of a technical nature such as miscoding and non-compliance with reporting requirements. The relative importance or seriousness of the problem cases that enter this data stream can vary from minor to major. Consequently, a second "filtering" step (block 156) is inserted into Data Stream C to select cases for further processing.

Described next is the further processing of cases in Data Stream A.

Block 150, Case Closure

Cases in which the data quality checking routines (block 146) failed to generate problem messages are sorted by the Problem Case Filter (block 148) into Data Stream A and submitted for case closure functions (block 150). Since no further processing is required for these cases, their data records are prepared for removal from active program files (i.e. these cases are "closed"). Depending upon the data transfer option chosen, the records for these cases may be returned to a host computer automatically via a computer-readable media such as computer tapes or diskettes, or a printed record of closed cases may be produced.

A record of the data quality status for these cases (i.e. the fact that no messages had been generated) is stored in a temporary file that is later used to generate profile reports.

At the conclusion of this step, the active case file is purged and the system is made ready to process another group of cases.

For cases that enter the case closure routine through Data Stream C-1, the same functions are performed. The single difference is that the data quality status information routed to the profile report file indicates that "low priority" data quality messages were generated rather than "no messages".

Block 152, Batch Printing and Logging of Worksheets (Data Stream B)

All cases routed to Data Stream B are destined for review by physicians since each had generated at least one data quality message of high priority that requires physician input to resolve. As the batch processing run proceeds, a file is created that temporarily stores relevant patient information and the message tests to be printed. Once all cases are processed, physician worksheets are printed for the entire group of cases. The actual printing of worksheets may be delayed for convenience at the user's option.

Simultaneously, as these worksheets are being produced, they are automatically logged by the system for later tracking to assure completion.

A listing of all worksheets assigned to physician reviewers (see block 38) is automatically generated to facilitate the logistics of the review process.

Block 154, Physician Worksheets for Cases with Potential Clinical Reporting

The content and format of Physician Worksheets have been specifically designed for communicating the physician reviewers messages that deal with potential clinical misrepresentation problems (see Table 1A). A sorting mechanism is employed to print on physician worksheets only those messages that deal with the clinical validity of reported claims data, requirements for substantiating documentation on the medical record, or issues that require medical judgment to resolve.

In the event that multiple messages are generated by a given case, all that meet the user's definition of a review case will be printed on the Physician Worksheet in the order they are generated. Conversely, no messages will be printed on the Physician Worksheet that:
a). fail to be of high enough priority for review cases, or
b). deal only with diagnosis or procedure coding or other technical reporting issues. Note, however, that messages which require the input and expertise of both coders and physicians will appear on both types of worksheets.

Block 156, Prioritize Cases for Review (Data Stream C)

Routed into Data Stream C by the Problem Case Filter are those cases that exhibit a significant potential for being miscoded, are in non-compliance with established reporting requirements, or that contain technical problems such as typographical errors. There is, however, considerable variance among the messages generated for cases in this data stream with regard to their seriousness or potential consequences. Some messages identify actual errors such as invalid diagnosis or procedure codes, unacceptable reporting sequences, or missing required data input. All cases that generate any absolute error messages of this kind are automatically recognized as high priority cases and are channeled into Data Stream C-2.

There is also a large number of messages that deal with potential problems in coding or reporting whose importance or actionable consequences may vary from major to minor. Accordingly, a capability has been added to the system that enables the user to prioritize which cases are to be selected for in-depth review. Typically, policy decisions determine what types of data quality issues are to receive review priority by third party surveillance organizations. Consequently, a mechanism is provided to enable the user to predetermine which potential problems in data quality are to be assigned high priority and thus would be channeled into Data Stream C-2 for further processing. Cases with messages of lower priority are channeled into Data Stream C-1 and routed to the case closure routine as previously described.

Block 158, Batch Printing and Logging of Worksheets

Operationally, this step is performed in a fashion identical to block 152. Typically, however, a turnaround worksheet of different format is generated (at the user's option) which is better suited for dealing with coding problems. The coding worksheet differs from the Physician Worksheet both in format and content as is described in block 160 and illustrated in Table 1.

Block 160, Coding Worksheets for Cases with Potential Miscoding or Technical Misreporting The coding worksheet has been designed to facilitate the process of making and recording corrections to the clinical data set. It is a two-part document with patient identifier data and data quality messages appearing on the first page and a pre-structured data correction matrix on the second page to capture all additions, corrections, or re-sequencing of diagnosis or procedure codes (see Table 1B).

This particular design of the coding worksheet is especially useful in supporting decentralized record review activities as it provides a mechanism for establishing reliable bilateral communications between data specialists and other personnel such as physician reviewers.

Block 162, Initial Profile Report (See FIG. 2)

This is an aggregate data report that characterizes the quality of the initial claims data reported for the group of cases under review. The distribution of data quality messages is displayed according to the source or cause of the problems encountered. The pattern depicted by this distribution reveals the existence of any systematic bias or repetitive error in claims data as reported by a given hospital or care provider. A section of this report separately identifies any pattern of systematic problems in data quality that may exist among cases whose diagnostic data have been sequenced to generate maximum payment levels.

Another section of this report is designed to assess overall data integrity for the entire group of cases analyzed. Under the label of a "veracity index", this calculation is defined as the ratio of unexploited opportunities to maximize claims payments divided by the total number of data quality messages. This ratio indicates the relative extent to which claims reporting has resisted bias in the direction of increasing payments of the hospital. The higher the number the greater is the evidence of unbiased claims reporting.

Block 164, Data Transfer Program

The data correction process that follows can be managed entirely as a manual process. Under this operational mode, the worksheets serve as the vehicle for communicating data clarification requests among review personnel, the case listing provides logistic support in the form of tank assignments, and the Initial Profile Report is useful in setting priorities for follow-up record review activities. There are operative conditions, however, which could make it desirable to conduct the data correction process in an interactive mode. For example, when data quality checks and worksheet printing are done at a central office location but follow-up review activities are subsequently conducted on-site at hospital locations, then interactive data quality analyses performed on a portable computer may be highly desirable.

To facilitate interactive data quality analyses and data corrections on portable computers, a special data transfer mechanism has been created. Upon making an option selection in the system utility program (see block 14), an appropriate set of patient data files and data quality status files are routed via a suitable electronic transfer medium such as a computer diskette and duplicate files are established within the portable computer. Case data may then be retrieved on the portable computer and processed interactively in support of follow-up review activities, such as data correction entries, data checks re-runs, and the printing of additional worksheets whenever relevant to guide the follow-up case review process.

Block 166, Record-based Case Review (Combined Data Streams B and C2)

The actual review of a medical record conducted in response to data quality messages is essentially a human activity and will remain so until the advent of fully automated ("paperless") medical records. Data specialists review the medical record in response to data quality messages printed on Coding Worksheets (see block 160) that address coding problems, incomplete or erroneous demographic data, and other technical aspects of hospital claims reporting.

In parallel, physicians review the medical record in response to data quality messages printed on Physician Worksheets (see block 154) that address record documentation and reporting issues involving clinical judgment. Typically, review coordinations pre-screen the messages on Physician Worksheets and append helpful focus notes that direct the physician reviewer's attention to specific entries in the medical record that are relevant to the issue(s) addressed in the message(s).

The physician reviewer then corrects the reported claims data by making additions or deletions, by restating the descriptive clinical term(s), or by resequencing them. Once the physician reviewer records corrections to the narrative terms on the Physician Worksheet, a coding specialist then recodes the terms in compliance with established coding guidelines. The corrected codes are then prepared for re-entry into the computer data base.

Block 168, Enter Corrections for Each Case, Check and Resolve All Messages

Most data corrections are made to diagnosis and procedure codes. Additions and re-sequencing of codes are common and the most frequently changed code is that for the principal diagnosis. Once such corrections are made on a given worksheet, the specific patient file is retrieved and the computer record is updated.

Upon completion of the data entry process, data quality checks are automatically run again. There are two reasons for the automatic initiation of data quality checks at this point in the review process: 1) with the correction of the more basic types of reporting errors, higher level (i.e. more sophisticated) reporting problems often become evident and 2) typographical errors or incongruities associated with the data correction process must be detected and resolved.

Block 170, Forward to Third-Party Data Base

No further data processing is needed when the third-party review organization maintains its own data base for capturing the results of the review activities. Consequently, the final corrected data set for each case would then be transferred to the sponsoring organization's data base via appropriate electronic media.

Block 172 (See Block 142)

Block 174, Perform Data Archive

When the Patient Data Quality Review System is operated in an environment in which the sponsoring third-party review organization does not maintain data files for storing the results of the data correction process, it is necessary to establish and maintain such a data base. The Data Archive Program consists of an integrated assembly of data processing transactions that performs three main functions (block 56): 1) Removal of completed patient records from the active patient file (i.e. file purging), 2) storage of patient records on an appropriate machine readable medium (i.e. archival storage of data), and 3) the generation of useful data summary reports from aggregated case data.

Operationally, data storage and file purging transactions usually take place as a single batch operation that is performed after all cases in a given group have completed the data correction process. Thus, this phase of the archive process typically is performed on a monthly or quarterly basis.

The generation of cumulative performance reports (see block 176) may be performed immediately upon the transfer of data to archival storage or may be performed independently at any time.

Block 176, Generate Cumulative Data Reports

Two different families of cumulative performance reports may be generated from archival data. From stored records of the initial and final DRG assignments, it is possible to calculate the impact on hospital payments of corrections made to reported claims data. One is a case-by-case listing which displays the initial and final DRG assignments and the resultant change in payment, if any. The second is a summary of the net revenue impact by payer for all cases in the archive file.

From records of the initial versus the final data quality status, summary reports of several types can be generated to characterize the impact of the data correction process on the quality of reported claims data (block 106). For third-party claims review organizations, System Activity Reports (see Table 7) and Data Quality Improvement reports (see Table 8) are the most relevant and useful.

While the best mode for carrying out the invention has been described in detail, those familiar with the art to which this invention relates will recognize various alternative designs and embodiments for practicing the invention as defined by the following claims.

What is claimed is:

1. In an automated patient data review system including a system memory, a program of instructions stored in the system memory, a processor coupled to the system memory and a system output device coupled to the processor, a method for automatically detecting, analyzing and classifying patient data reported on a plurality of payment claims, the method comprising the steps of:

storing collections of patient data including patient identifiers and clinical data, misreporting tables and message tables in data files in the system memory;

storing classification data and case review tables in the data files in the system memory; and automatically processing a plurality of patient cases, the step of processing the patient cases being performed by the processor in accordance with the program of instructions and including the steps of:

determining whether misreporting conditions exist in the stored clinical data, the misreporting conditions including actual or potential non-compliance with federally mandated coding and reporting rules and actual or potential failure to properly report complexities of the case;

generating at least one data quality message based upon the misreporting tables, the message tables and the determined misreporting conditions;

classifying the data quality messages generated for a case based upon the probability and relative seriousness or consequences of noncompliance with federal coding and reporting rules or the failure to report case complexities adequately;

displaying via the system output device the patient data including the patient identifiers and the clinical data;

displaying via the system output device at least one message based on the determined misreporting conditions in the patient data;

automatically accumulating aggregate case data and system analysis data on a plurality of patient cases and storing the aggregate case data and system analysis data in system data files in the system memory;

automatically analyzing the aggregate case data in order to identify patterns of aggregate case data; and generating at least one analysis report for a plurality of patient cases based upon the analyzed aggregate case data.

2. The method as claimed in claim 1 wherein a plurality of data quality messages are generated and wherein the method further comprises the step of classifying the data quality messages.

3. The method as claimed in claim 2 wherein the step of classifying the data quality messages is performed in an hierarchical manner.

4. The method as claimed in claim 1 wherein the step of classifying each case is performed in an hierarchical manner.

5. The method as claimed in claim 1 wherein the step of classifying each case is based on the type of the determined misreporting condition.

6. The method as claimed in claim 1 wherein the step of classifying data quality messages generated for a case includes determining a probably cause of the misreporting conditions.

7. The method as claimed in claim 1 wherein the step of classifying each case is based on the consequences of the determined misreporting condition.

8. The method as claimed in claim 1 wherein the step of classifying the data quality messages for a case is based on user-defined prioritization criteria.

9. The method as claimed in claim 1 wherein the step of displaying patient data includes the step of presenting the patient data in a final, reportable form.

10. The method as claimed in claim 9 wherein the patient data are presented for each patient case.

11. The method as claimed in claim 9 wherein the patient data are presented in aggregate form for the plurality of patient cases.

12. The method as claimed in claim 1 wherein the step of displaying the at least one message includes the step of displaying the at least one message for each patient case.

13. The method as claimed in claim 11 wherein the step of displaying the at least one message includes the step of presenting the at least one message for each case in aggregate form for the plurality of patient cases.

14. The method as claimed in claim 12 further comprising the steps of routing the at least one message to appropriate personnel by comparing the classification results to selection criteria and displaying the at least one message via a system output device.

15. The method as claimed in claim 14 wherein the at least one message is an alternative message text stored in the data files that is appropriate in orientation, vocabulary, and format to the professional status of the appropriate personnel.

16. The method as claimed in claim 9 wherein the step of displaying patient data includes the step of displaying messages corresponding to determined misreporting conditions concurrently with the step of presenting.

17. The method as claimed in claim 1 wherein the data files contain patient data and systems analysis data which includes personnel performance data representing an assessment of trends in personnel efficiency and effectiveness of data correction activities in response to messages routed to appropriate personnel.

18. The method as claimed in claim 1 wherein the step of storing classification data and review tables in the data files includes the steps of entering and storing user-defined alternatives for diagnosis titles, procedure titles, DRG titles, and DRG cost weights to be accessed at user option in data displays.

19. The method as claimed in claim 1 wherein the step of determining whether misreporting conditions exist includes the step of determining whether a reporting sequence of the clinical data has resulted in a maximum achievable payment under a DRG-based payment mechanism.

20. The method as claimed in claim wherein the step of determining whether misreporting conditions exist includes the step of determining the likelihood of truthfulness in reporting of claim data for a plurality of patients by quantifying unexploited opportunities to increase payment via the reporting of alternative diagnoses and procedure terms.

21. The method as claimed in claim 17 further comprising the step of exchanging data with at least one automated data system.

22. The method as claimed in claim 17 wherein the step of automatically accumulating the aggregate case data and the system analysis data including the personnel performance data includes the step of accumulating summary statistics related to the aggregate case data and the system analysis data across reporting periods.

23. The method as claimed in claim, 17 wherein the step of generating the at least one analysis report includes the step of creating descriptive profiles from the aggregate case data, and system analysis data including the personnel performance data accumulated from a plurality of patients.

24. The method as claimed in claim 23 further comprising the step of characterizing the quality of patient data as to the type of data quality message generated.

25. The method as claimed in claim 23 further comprising the step of characterizing problems encountered with respect to the quality of the patient data based on the source of the patient data.

26. The method as claimed in claim, 14 further comprising the step of characterizing the impact of changes in patient data on payments based upon DRG assignments and payments.

27. The method as claimed in claim 17 wherein the step of generating the at least one analysis report includes the step of creating at least one comparison report from the aggregate case data, and the system analysis data including the personnel performance data from a plurality of patients.

28. The method as claimed in claim 27 further comprising the step of comparing data contained on the comparison report from a given hospital with data contained on a comparison report from another hospital.

29. The method as claimed in claim 27 further comprising the step of comparing data contained in the comparison report from a given hospital with averaged data based on the data contained in the group of comparison reports from a group of hospitals.

30. The method as claimed in claim 27 further comprising the step of comparing data contained in the comparison report from a given hospital with normative data.

31. The method as claimed in claim 27 further comprising the step of comparing data contained in the comparison report from a given hospital claims payer with data contained in a comparison report of another payer.

32. The method as claimed in claim 27 further comprising the step of comparing data contained in the comparison report from a given hospital claims payer with average data based in the data contained in a group of comparison reports from a group of payers.

33. The method as claimed in claim 1 wherein the step of generating at least one analysis report includes the step of creating time trend analyses from aggregated case data, and system analysis data including personnel performance data accummulated in the form of summary statistics.

34. The method as claimed in claim 33 wherein the time trend analyses include descriptive patient data compared across reporting periods.

35. The method as claimed in claim 33 wherein the time trend analyses include descriptive profiles of data quality compared across reporting periods.

36. The method as claimed in claim 33 wherein the time trend analyses include system activities compared across reporting periods.

37. The method as claimed in claim 33 wherein the time trend analyses include personnel performance compared across reporting periods.

38. The method as claimed in claim 33 wherein the time trend analyses include changes in payment levels to hospitals by payers compared across reporting periods.

39. A program storage device readable by a machine, tangibly embodying a program of instructions executable by the machine to perform the method steps of any of claims 1 through 38.

40. A system for automatically detecting, analyzing and classifying patient data reported on a plurality of payment claims, the system comprising:
   a program of instructions for detecting, analyzing and classifying patient data;
   a system memory for storing the program of instructions, data files of collections of patient data including patient identifiers and clinical data, misreporting tables and message tables, and classification data and case review tables;
   a processor coupled to the system memory to carry out the program of instructions for:
      determining whether misreporting conditions exist in the stored clinical data, the misreporting conditions including actual or potential non-compliance with federally mandated coding and reporting rules and actual or potential failure to properly report complexities of the case;
      generating at least one data quality message based upon the misreporting tables, the message tables and the determined misreporting conditions;
      classifying the data quality message generated for each case based upon the classification data, the review tables and the determined misreporting conditions to obtain classification results;
      automatically accumulating aggregate case data and system analysis data on a plurality of patient cases and storing the aggregate case and system analysis data in system data files; and
      automatically analyzing the aggregate case data in order to identify patterns of aggregate case data;
   and a system output device coupled to the processor for:
      displaying the patient data including the patient identifiers and the clinical data;
      displaying at least one message based on the determined misreporting conditions in the patient data; and
      generating at least one analysis report for a plurality of patient cases based upon the analyzed aggregate case data.

41. The system as claimed in claim 40 wherein a plurality of data quality messages are generated and wherein the processor classifies the data quality messages.

42. The system as claimed in claim 41 wherein the processor classifies the quality messages in an hierarchical manner.

43. The system as claimed in claim 40 wherein the processor classifies each case in an hierarchical manner.

44. The system as claimed in claim 40 wherein the processor classifies each case based on the type of the determined misreporting condition.

45. The system as claimed in claim 40 wherein the processor classifies data quality messages generated for a case includes determining a probable cause of the misreporting conditions.

46. The system as claimed in claim 40 wherein the processor classifies each case based on the consequences of the determined misreporting condition.

47. The system as claimed in claim 40 wherein the processor classifies the data quality messages for a case based on the user-defined prioritization criteria.

48. The system as claimed in claim 40 wherein the system output device presents the patient data in a final, reportable form.

49. The system as claimed in claim 48 wherein the patient data are presented for each patient case.

50. The system as claimed in claim 48 wherein the patient data are presented in aggregate form for the plurality of patient cases.

51. The system as claimed in claim 40 wherein the system output device displays the at least one message for each patient case.

52. The system as claimed in claim, 50 wherein the system output device presents the at least one message for each case in aggregate form for the plurality of patient cases.

53. The system as claimed in claim 51 further comprising means for routing the at least one message to appropriate personnel, the means for routing comparing the classification results to selection criteria and wherein the system output device displays the at least one message.

54. The system as claimed in claim 53 wherein the at least one message is an alternative message text stored in the data files that is appropriate in orientation, vocabulary, and format to the professional status of the appropriate personnel.

55. The system as claimed in claim 48 wherein the system output device displays messages corresponding to determined misreporting conditions concurrently with presenting the patient data.

56. The system as claimed in claim 40 wherein the system analysis data includes personnel performance data representing an assessment of trends in personnel efficiency and effectiveness of data correction activities in response to messages routed to appropriate personnel.

57. The system as claimed in claim 40 wherein the system memory stores user-defined alternatives for diagnosis titles, procedure titles, DRG titles, and DRG cost weights to be accessed at user option in data displays.

58. The system as claimed in claim 40 wherein the processor determines whether a reporting sequence of the clinical data has resulted in a maximum achievable payment under a DRG-based payment mechanism.

59. The system as claimed in claim 40 wherein the processor determines the likelihood of truthfulness in reporting of claim data for a plurality of patients by quantifying unexploited opportunities to increase payment via the reporting of alternative diagnoses and procedure terms.

60. The system as claimed in claim 56 wherein the processor exchanges data with at least one automated data system.

61. The system as claimed in claim 56 wherein the processor accumulates summary statistics related to the aggregate case data and the system analysis data across reporting periods.

62. The system as claimed in claim 56 wherein the processor creates descriptive profiles from the aggregate case data, and system analysis data including the personnel performance data accumulated from a plurality of patients.

63. The system as claimed in claim 62 wherein the processor characterizes the quality of patient data as to the type of data quality message generated.

64. The system as claimed in claim 62 wherein the processor characterizes problems encountered with respect to the quality of the patient data based on the source of the patient data.

65. The system as claimed in claim 53 wherein the processor characterizes the impact of changes in patient data on payments based upon DRG assignments and payments.

66. The system as claimed in claim 56 wherein the system output device creates at least one comparison report from the aggregate case data, and the system analysis data including the personnel performance data from a plurality of patients.

67. The system as claimed in claim 66 wherein the processor compares data contained on the comparison report from a given hospital with data contained on a comparison report from another hospital.

68. The system as claimed in claim 66 wherein the processor compares data contained in the comparison report from a given hospital with averaged data based on the data contained in the group of comparison reports from a group of hospitals.

69. The system as claimed in claim 66 wherein the processor compares data contained in the comparison report from a given hospital with normative data.

70. The system as claimed in claim 66 wherein the processor compares data contained in the comparison report from a given hospital claims payer with data contained in a comparison report of another payer.

71. The system as claimed in claim 66 wherein the processor compares data contained in the comparison report from a given hospital claims payer with average data based in the data contained in a group of comparison reports from a group of payers.

72. The system as claimed in claim 40 wherein the processor creates time trend analyses from aggregated case data, and system analysis data including personnel performance data accummulated in the form of summary statistics.

73. The system as claimed in claim 72 wherein the time trend analyses include descriptive patient data compared across reporting periods.

74. The system as claimed in claim 72 wherein the time trend analyses include descriptive profiles of data quality compared across reporting periods.

75. The system as claimed in claim 72 wherein the time trend analyses include system activities compared across reporting periods.

76. The system as claimed in claim 72 wherein the time trend analyses include personnel performances compared across reporting periods.

77. The system as claimed in claim 72 wherein the time trend analyses include changes in payment levels to hospitals by payers compared across reporting periods.

* * * * *

UNITED STATES PATENT AND TRADEMARK OFFICE
CERTIFICATE OF CORRECTION

PATENT NO. : 5,307,262
DATED : April 26, 1994
INVENTOR(S) : Paul Y. Ertel

It is certified that error appears in the above-identified patent and that said Letters Patent is hereby corrected as shown below:

Column 2, lines 57 and 58
after "system which", replace "Verifies" with --verifies--;
    Column 3, line 6 after "disagree,", delete ".";
    Column 3, line 24
after "Dornbush", insert --et al.--;

Column 15, lines 6 and 7
after "into this" replace "film" with --file--;
    Column 15, line 52
after "Block", replace "53" with --52--;
    Column 22 TABLE 5
after TABLE 5" line 2 should read --Report date: 12/20/90--;
    Column 22, TABLE 5
for patient "_____, Doris" under "DOA", "11/12/90" should be --11/26/90--;

UNITED STATES PATENT AND TRADEMARK OFFICE
CERTIFICATE OF CORRECTION

PATENT NO. : 5,307,262
DATED : April 26, 1994
INVENTOR(S) : Paul Y. Ertel

It is certified that error appears in the above-identified patent and that said Letters Patent is hereby corrected as shown below:

Column 25 TABLE 8, line 14
    In the heading, before "Cases w Data Changes" replace "Realtive" with --Relative--;
    Column 31, line 50
after "a risk" replace "or" with --of--;
    Column 31, line 53
after "(block" replace "12" with --120--)

after "whether the" replace "cass" with --cases--;
    Column 37, line 52
after "that" replace "re" with --are--;
    Column 44, line 9
        after "claim" insert --1--; and

UNITED STATES PATENT AND TRADEMARK OFFICE
CERTIFICATE OF CORRECTION

PATENT NO. : 5,307,262

DATED : April 26, 1994

INVENTOR(S) : Paul Y. Ertel

It is certified that error appears in the above-indentified patent and that said Letters Patent is hereby corrected as shown below:

Column 44, line 25 (claim 23, page 98, line 22) after "claim" and before "17" delete ",".

Signed and Sealed this

Twenty-fifth Day of October, 1994

Attest:

BRUCE LEHMAN

Attesting Officer

Commissioner of Patents and Trademarks